United States Patent
Xiao et al.

(10) Patent No.: US 12,416,019 B2
(45) Date of Patent: *Sep. 16, 2025

(54) EXPRESSION CASSETTE CONTAINING OVERLAPPING OPEN READING FRAMES AND APPLICATION

(71) Applicant: GENEVOYAGER (WUHAN) CO., LTD., Hubei (CN)

(72) Inventors: He Xiao, Hubei (CN); Xiaobin He, Hubei (CN); Gang Huang, Hubei (CN); Xing Pan, Hubei (CN); Yicheng Zhou, Hubei (CN); Liang Du, Hubei (CN); Mengdie Wang, Hubei (CN); Huanhuan Zuo, Hubei (CN); Hao Sun, Hubei (CN)

(73) Assignee: GENEVOYAGER (WUHAN) CO., LTD., Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/434,746

(22) Filed: Feb. 6, 2024

(65) Prior Publication Data

US 2025/0043307 A1 Feb. 6, 2025

Related U.S. Application Data

(63) Continuation of application No. PCT/CN2023/141032, filed on Dec. 22, 2023.

(30) Foreign Application Priority Data

Aug. 3, 2023 (CN) .......................... 202310975187.6
Nov. 17, 2023 (CN) .......................... 202311544887.6

(51) Int. Cl.
*C12N 15/86* (2006.01)
*C12N 5/07* (2010.01)

(52) U.S. Cl.
CPC ............ *C12N 15/86* (2013.01); *C12N 5/0601* (2013.01); *C12N 2710/14022* (2013.01); *C12N 2710/14043* (2013.01); *C12N 2710/14052* (2013.01); *C12N 2750/14144* (2013.01)

(58) Field of Classification Search
CPC .................................................... C12N 15/86
See application file for complete search history.

(56) References Cited

FOREIGN PATENT DOCUMENTS

| CN | 101522903 | 9/2009 |
|----|-----------|--------|
| CN | 103849629 | 6/2014 |
| CN | 106544325 | 3/2017 |
| CN | 112553257 | 3/2021 |
| CN | 113897396 | 1/2022 |

OTHER PUBLICATIONS

Chen H. (2008, Molecular Cell Therapy, vol. 16(5), pp. 924-930). (Year: 2008).*
Pyle et al. (1997, Analytical Biochemistry, vol. 253, pp. 253-258). (Year: 1997).*
Urabe et al. (Human Gene Therapy, vol. 13, pp. 1935-1943). (Year: 2002).*
Seppo Ylä-Herttuala, "Endgame: glybera finally recommended for approval as the first gene therapy drug in the European union", Molecular Therapy, Oct. 2012, pp. 1831-1832.
Masashi Urabe et al., "Insect Cells as a Factory to Produce Adeno-Associated Virus Type 2 Vectors", Human Gene Therapy, Nov. 2002, pp. 1935-1943.
Masashi Urabe et al., "Scalable Generation of High-Titer Recombinant Adeno-Associated Virus Type 5 in Insect Cells", Journal of Virology, Feb. 2006, pp. 1874-1885.
Erik Kohlbrenner et al., "Successful Production of Pseudotyped rAAV Vectors Using a Modified Baculovirus Expression System", Molecular Therapy, Dec. 2005, pp. 1217-1225.
Xiao Xiao et al., "Production of High-Titer Recombinant Adeno-Associated Virus Vectors in the Absence of Helper Adenovirus", Journal of Virology, Mar. 1998, pp. 2224-2232.
Mark R. Bruder et al., "Utility of Alternative Promoters for Foreign Gene Expression Using the Baculovirus Expression Vector System", Viruses, Nov. 2022, pp. 1-18.

* cited by examiner

Primary Examiner — Anoop K Singh
Assistant Examiner — David A Montanari
(74) Attorney, Agent, or Firm — JCIPRNET

(57) ABSTRACT

An expression cassette containing overlapping open reading frames and an application thereof are provided. The overlapping open reading frames are overlapping open reading frames of a first ORF and a second ORF and include in sequence from a 5' end to a 3' end: a first promoter at least used to drive gene transcription of the first ORF; a 5' part of a gene of the first ORF; an intron; and a 3' part of a gene of the second ORF, the intron including a second promoter used only to drive gene transcription of the second ORF. By arranging two promoters in a single expression cassette in the disclosure, the two promoters are used to drive the expression of proteins of the overlapping reading frames and regulate the relative expression time and expression intensity of different proteins.

21 Claims, 10 Drawing Sheets
Specification includes a Sequence Listing.

EXPRESSION CASSETTE CONTAINING OVERLAPPING OPEN READING FRAMES AND APPLICATION

CROSS-REFERENCE TO RELATED APPLICATION

This application is a continuation of international application of PCT application serial no. PCT/CN2023/141032, filed on Dec. 22, 2023, which claims the priority benefit of China application no. 202310975187.6, filed on Aug. 3, 2023 and China application no. 202311544887.6, filed on Nov. 17, 2023. The entirety of each of the above-mentioned patent applications is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Jan. 29, 2024, is named 142172_SEQUENCELISTING and is 61,181 bytes in size.

BACKGROUND OF THE INVENTION

Technical Field

The disclosure belongs to the field of genetic engineering, and more specifically, relates to an expression cassette containing a gene with overlapping open reading frames and an application.

Description of Related Art

Adeno-associated virus (AAV), also known as adeno-accompanied virus, belongs to the genus Dependentvirus in the family Parvoviridae, is the single-stranded DNA-deficient virus with the simplest structure discovered so far, and requires helper viruses (usually adenoviruses) to participate in replication. The AAV genome is a single-stranded linear DNA, approximately 4700 bp, and includes two upstream and downstream open reading frames (ORFs): Rep and Cap, located between 2 T-shaped inverted terminal repeats (ITR) composed of 145 nucleotides each, as shown in FIG. 1. The function of ITR is to serve as the origin of viral replication and packaging signal. The Rep gene is involved in viral replication and integration and encodes viral replication proteins. The Cap gene is responsible for encoding the three capsid proteins of the virus. Recombinant adeno-associated virus (rAVV) is one of the most promising vectors in the field of gene therapy due to its characteristics of wide host range, low immunogenicity, high safety, and capability of mediating long-term stable expression of exogenous genes in animals. With the approval of the first recombinant adeno-associated virus (rAAV)-mediated gene therapy, there is increasing demand for large-scale AAV vector manufacturing technology (Yla-Herttuala S., 2012, Mol Ther, 20:1831-1832).

At present, there are two main types of rAAV production systems: one is a conventional production system using mammalian cells (e.g., 293 cells, COS cells, HeLa cells, KB cells, etc.), and the other is a production system using insect cells. Herein, the production system using insect cells uses the baculovirus expression vectors (BEVs) carrying the rAAV vector genome, Rep protein, and Cap protein to infect Sf9 insect cells to produce rAAV virus. Taking advantage of the fact that Sf9 cells can express large amounts of recombinant proteins, this system uses insect baculovirus containing rAAV genome, AAV-Rep, and AAV-Cap genes to transduce Sf9 cells, allowing rAAV to be assembled in Sf9 cells, and the purpose of large-scale production of rAAV is ultimately achieved.

In this production system, promoters play an important role. The selected exogenous gene is placed under the control of a native promoter and then expressed during the infection cycle, releasing the protein during cell lysis. The promoter is recognized by RNA polymerase, and transcription begins. In ribonucleic acid (RNA) synthesis, the promoter can interact with the transcription factor that determines the start of transcription, controls the initiation time and extent of gene expression (transcription). It contains the core promoter region and the regulatory region, which is like a "switch" that determines the activity of the gene and thus controls which protein the cell starts to produce. The promoter itself has no compilation function, but it has the function of directing the translation of amino acids in the gene, just like a flag. The core part thereof is the RNA polymerase binding site upstream of the non-coding region. Currently, the most commonly used promoters in BEVS are the polyhedral pol H (polyhedrin) promoter and the p10 promoter, in addition to basic promoters and a few early promoters. The expression levels of the same exogenous gene under the control of different promoters are greatly different.

In order to achieve maximum expression levels, very late promoters are used most of the time to drive the expression of exogenous genes. Although this approach is usually successful when large amounts of recombinant protein are required, but in some cases, the use of alternative promoters with earlier or weaker expression may be beneficial to the quality and yield of the final protein. Proteins that aggregate during rapid expression and proteins that require advanced post-translational modifications have also been shown to yield ideal products through sustained and stable expression using early promoters.

Immediate early and early promoters are activated prior to viral DNA replication. The immediate early promoter (IE) is transcribed by host cell RNA polymerase II and also utilizes host transcription factors. The structural organization of the immediate early and early promoters is quite different from that of the late and very late baculovirus promoters, and is more similar to that of other eukaryotic promoters. The most striking feature of the baculovirus immediate early promoter is the conserved CAGT motif, which serves as the transcription start site and plays an important role in regulating downstream gene expression. In some cases, immediate early promoter contains a TATA-like motif and/or an initiation sequence. This region is recognized by host RNA polymerase II and allows transcription of immediate early viral genes immediately following infection. The IE1 promoter is an immediate early promoter and is the most commonly used constitutive promoter for baculovirus expression because it is active at all time stages as well as in uninfected insect cells. The 39 k promoter is an early promoter that is transactivated by the IE1 protein. When being co-expressed with the IE1 protein, the 39 k promoter can also be used transiently.

The late promoter is transcribed by a viral RNA polymerase that recognizes the conserved (A/G/T) TAAG late/very late promoter motif. The transcription initiates at the second nucleotide within this motif, and its presence is required for promoter activity. Studies investigating the function of the TAAG motif in late promoters have shown that mutations in this sequence disrupt promoter transcriptional activity. The very late promoter transcriptional activity peaks at 18 to 24 hours after infection and exceeds late promoter activity. At 24 hours after infection, the transcription level of the very late promoter exceeds that of all other promoters in cells.

The P10 protein is expressed at high levels very late in the infection cycle and is thought to play a role in inclusion maturation and cell lysis required for virus release. Weyer and Possee first define the 101 nucleotides upstream of the ATG of the p10 gene as the p10 promoter sequence and suggest that it be used for the expression of exogenous proteins. Since then, the p10 promoter has been widely used to produce proteins in BEVS, such as the production of cauliflower mosaic virus gene 1 and human interleukin 2. p10 can also be used to connect other promoters for co-expression.

In the AAV insect cell production system, for the Cap protein, Urabe et al. replace the start codon AUG of VP1 with the suboptimal start codon ACG to construct one single polycistronic mRNA. This polycistronic mRNA expresses all three AAV2 VP proteins without the need for splicing (Urabe et al., 2002, Hum Gene Ther, 13:1935-1943). However, there are many and increasing serotypes of AAV, and the modification method of Urabe et al. is not suitable for all serotypes. For instance, AAV5 particles produced in the baculovirus system of Urabe et al. using ACG as the start codon of the VP1 capsid protein have poor infectivity. In the method provided by Chinese patent CN106544325A, different suboptimal start codons CTG are used to enhance the expression of VP1. Although this design improves the infectivity of AAV5 particles, this method lacks flexibility in adjusting the relative content of VP1/VP2/VP3. Further, this method also appears to lack the flexibility necessary for serotype-specific sequence adjustment. In the method provided by Chinese patent CN101522903A, an artificial intron containing the polH promoter sequence is inserted into the open reading frame of VP1, and two promoters are used to express VP1 and VP2/VP3. Although this design can also achieve the expression of VP1/VP2/VP3 in the same reading frame, this method cannot effectively adjust the relative amounts of VP1/VP2/VP3. Moreover, the relative expression amounts of VP1/VP2/VP3 vary greatly among different serotypes, resulting in low production efficiency.

For the expression of the Rep protein, Urabe et al. construct two independent expression cassettes containing Rep78 and Rep52 and inserted them into the same baculovirus vector. Herein, Rep52 uses the polH promoter, and Rep78 uses the deltaIE1 promoter, which has weaker promoter activity than the polH promoter (Urabe et al., 2002, Hum Gene Ther, 13:1935-1943). However, the immediate early promoter deltaIE1 is active early in baculovirus infection, and early and abundant expression of the Rep78 protein in insect cells may have a negative impact on the yield of recombinant baculovirus (Urabe et al., 2006, Journal of Virology 80.4:1874-1885). Further, some studies have found that the AAV Rep protein expression method developed by Urabe et al. has the problem of unstable passaging of baculovirus vectors (Kohlbrenner et al., 2005, Mol. Ther.12: 1217-25). In order to solve the problem of inherent passaging instability of two independent Rep expression cassettes, Chinese patent CN 103849629 A discloses a method for producing AAV in insect cells. The translation initiation codons of the AAV Rep78 protein is replaced with ACG, and the codon is partially skipped by scanning ribosomes so that the translation initiation can also occur at the start codon of the Rep52 protein further downstream. In this method, the expression of Rep78 and Rep52 proteins in the same reading frame can be achieved, and the stability of the rAAV vector produced in insect cells is significantly improved. However, this method lacks flexibility in adjusting the relative contents of Rep52/Rep78 proteins. The high stoichiometric ratio of Rep52/Rep78 proteins may be a key factor in the high yield of rAAV (Xiao, Xiao et al., 1998, Journal of Virology 72.3 (1998): 2224-2232). In a method for producing AAV in an insect cell disclosed in Chinese patent CN 113897396 A, the inventors achieve the expression of Rep78 and Rep52 proteins in the same reading frame by constructing a Rep expression cassette containing an intron regulatory sequence. In this way, the stability of the rAAV vector produced in the insect cell is improved, and further, the relative content of Rep52/Rep78 proteins can be flexibly adjusted by adjusting the intron splicing efficiency. However, there is a lack of flexibility in controlling the relative expression time and relative expression intensity of the two.

Therefore, the large-scale production of rAAV vectors using baculovirus in insect cells still needs to be further improved. Many studies have shown that earlier promoters may be more efficient in producing some exogenous proteins, particularly those that require extensive post-translational processing and/or secretion. This is because when the latest promoter is most active, the host cell's processing of the exogenous protein may be impaired. For complex viral particles, different proteins may be required in different amounts. By using different baculovirus promoters that are active at different stages of infection, control of the expression time and amount of the target protein can be achieved (Bruder et al., Viruses 2022, 14, 2670). However, the mechanism of synergy between different promoters is still unclear.

SUMMARY OF THE INVENTION

In view of the above defects or improvement needs of the related art, the disclosure provides an expression cassette for a gene containing overlapping open reading frames and an application, aiming to better control the relative expression time and relative intensity of different proteins represented by Rep78 and Rep52 proteins by constructing an expression cassette containing different proteins located in the same overlapping open reading frame and by using different promoters to control the expression of different proteins, and the use of overlapping open reading frames to express proteins not only ensures the stability of a rAAV vector produced an in insect cell, but also improves the yield and quality of the produced rAAV.

To achieve the above, in an aspect of the disclosure, the disclosure provides an expression cassette of a gene containing overlapping open reading frames, including:
  operably linked from a 5' end to a 3' end:
  an artificially constructed sequence; and
  an overlapping open reading frame lacking a first translation initiation codon,
  where the artificially constructed sequence includes a first promoter and a second promoter independent of each other, and a complete sequence of the first translation initiation codon is not included between the first promoter and the second promoter.

Preferably, the gene is a parvovirus Rep gene, the first promoter is used to drive expression of a Rep78/68 protein and a Rep52/40 protein, and the second promoter is used to additionally drive the expression of the Rep52/40 protein.

Preferably, the gene is a parvovirus Cap gene, the first promoter is used to drive expression of a VP1 protein and a VP2/3 protein, and the second promoter is used to additionally drive the expression of the VP2/3 protein.

Preferably, the artificially constructed sequence further includes an intron, and the intron is used to form the first translation initiation codon in the artificially constructed sequence through alternative splicing during post-transcriptional processing.

Further preferably, the intron is located between any two nucleotides of ATG.

Further preferably, the first promoter precedes the 5' end of the intron.

Further preferably, the second promoter is within the intron.

Preferably, the second promoter precedes the 5' end of the first promoter.

Preferably, the first promoter is active before the second promoter.

Further preferably, the first promoter is deltaIE1, IE1, 39K, or p6.9, and the second promoter is polH or p10.

Preferably, the first promoter is p10, and the second promoter is polH.

According to an aspect of the disclosure, the disclosure provides an optimized expression cassette for a gene containing overlapping open reading frames. The overlapping open reading frames are overlapping open reading frames of a first ORF and a second ORF and further include in sequence from a 5' end to a 3' end:
  a first promoter used to drive gene transcription of the first ORF;
  a 5' part of a gene of the first ORF;
  an intron; and
  a 3' part of a gene of the second ORF,
  where the intron includes a second promoter used to drive gene transcription of the second ORF, the first promoter is an immediate early promoter, an early promoter, or a late promoter, and the second promoter is a very late promoter.

Preferably, the intron is located between any two nucleotides of the translation initiation codons ATG of the first ORF. The intron is used to form the first translation initiation codon in the artificially constructed sequence through alternative splicing during post-transcriptional processing.

Preferably, the intron is located between the translation initiation codons ATG of the first ORF and an exon of the first ORF.

Preferably, the first promoter is deltaIE1, IE1, 39K, or p6.9, and the second promoter is polH or p10.

Preferably, the expression cassette is used to encode a parvovirus Rep gene, the first ORF is used to encode a Rep68/Rep78 protein, and the second ORF is used to encode a Rep40/Rep52 protein.

Preferably, the expression cassette is used to encode a parvovirus Cap gene, the first ORF is used to encode a VP1 protein, and the second ORF is used to encode a P2/VP3 protein.

According to another aspect of the disclosure, the disclosure further provides a nucleic acid molecule including a first expression cassette, and the first expression cassette is any expression cassette of the above.

Preferably, a second expression cassette is further included, and the first expression cassette and the second expression cassette are respectively used to encode the parvovirus Cap gene and the parvovirus Rep gene.

Preferably, the nucleic acid molecule further includes an exogenous gene.

Further preferably, AAV inverted terminal repeats are provided at both ends of the exogenous gene.

Further preferably, the exogenous gene is a reporter gene, and the reporter gene is at least one of a chloramphenicol acetyltransferase encoding gene, a β-galactosidase encoding gene, a β-glucuronidase encoding gene, a *Renilla* luciferase encoding gene, an alkaline phosphatase encoding gene, a firefly luciferase encoding gene, a green fluorescent protein encoding gene, and a red fluorescent protein encoding gene.

Further preferably, the exogenous gene is a gene encoding a drug polypeptide, and the drug polypeptide is at least one of lipoprotein esterase, apolipoprotein, cytokine, interleukin, and interferon.

According to another aspect of the disclosure, the disclosure further provides a recombinant baculovirus vector including the expression cassette according to the above.

Preferably, the recombinant baculovirus vector is an insect cell compatible vector.

According to another aspect of the disclosure, the disclosure further provides an insect cell including the recombinant baculovirus vector according to the above.

Preferably, the insect cell is a *Spodoptera frugiperda* cell, a *Trichopodia* cell, a *Drosophila* cell, or a mosquito cell.

To sum up, in the technical solutions provided by the disclosure when being compared to the related art, two promoters are arranged in a single expression cassette to drive the expression of proteins of the overlapping reading frames and regulate the relative expression time and expression intensity of different proteins. The relative expression time and a wider range of relative expression intensity of the Rep78/68 protein and the Rep52/40 protein in the Rep gene, as well as the relative expression time and a wider range of relative expression intensity of the VP1 protein and the VP2/3 protein in the Cap gene can be better controlled in the disclosure. In this way, not only the efficiency of rAAV vector production in the insect cell is improved, but also the quality of the produced AAV is improved.

DETAILED DESCRIPTION OF THE EMBODIMENTS

Figure 1:
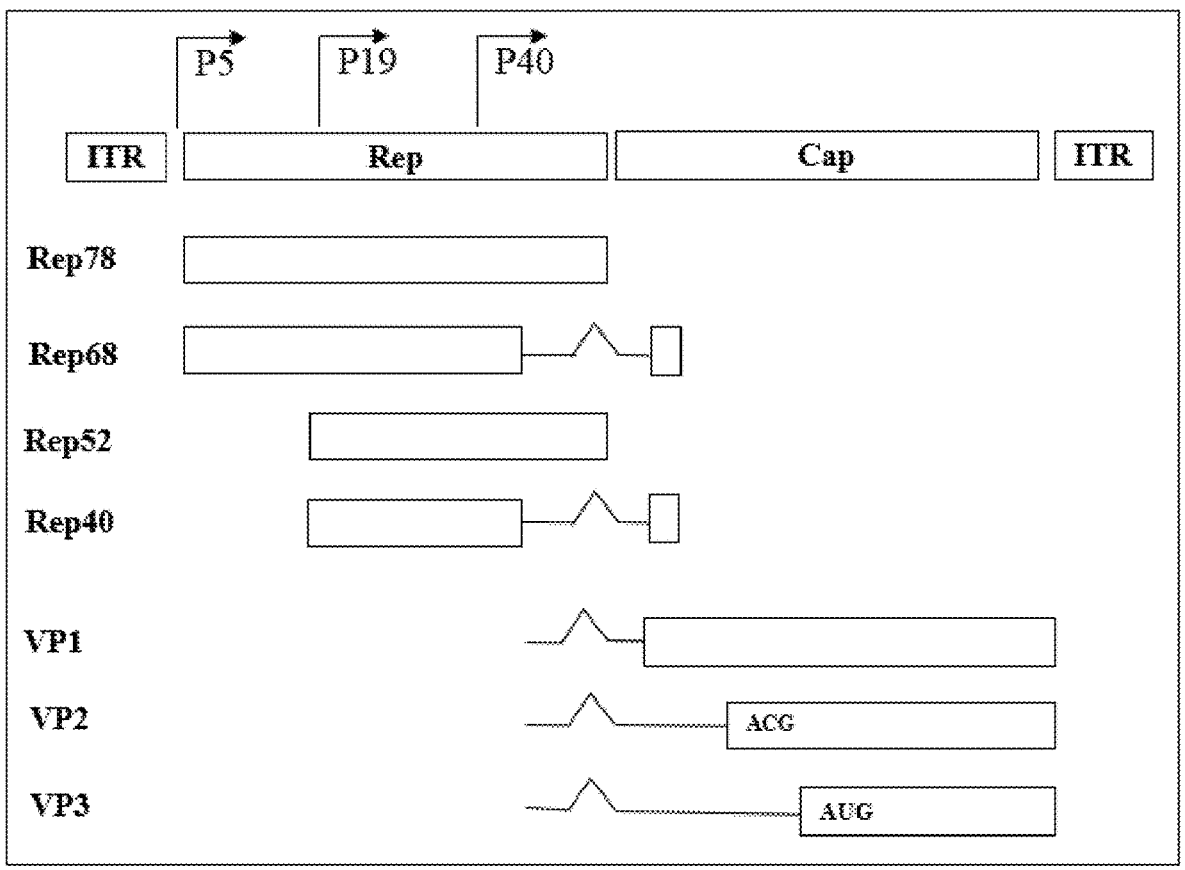
FIG. 1 is a schematic diagram of expression regulation of a Cap gene and a Rep gene in wild-type AAV.

In order to make the objectives, technical solutions, and advantages of the disclosure clearer and more comprehensible, the disclosure is further described in detail with reference to the drawings and embodiments. It should be understood that the specific embodiments described herein serve to explain the invention merely and are not used to limit the invention. In addition, the technical features involved in the various embodiments of the invention described below can be combined with each other as long as the technical features do not conflict with each other.

For ease of understanding, the terms appearing in this specific embodiment are defined as follows:

The term "polynucleotide": refers to a biological macromolecule composed of single nucleotides. The polynucleotide molecule mentioned in the disclosure may be a deoxyribonucleic acid (DNA) molecule or a ribonucleic acid (RNA) molecule. A person having ordinary skill in the art knows that the RNA sequence is basically similar to the DNA sequence or has a certain degree of sequence identity. Thymine (T) in the DNA sequence can be considered equivalent to uracil (U) in the RNA sequence.

The term "operably linked": refers to the connection of polynucleotide (or polypeptide) sequences in a functional relationship. Two nucleotide sequences are "operably linked" when the two nucleotide sequences are placed in a functional relationship. For instance, a transcriptional control sequence (e.g., a promoter) is operably linked to a gene's coding sequence if it affects the transcription of the gene's coding sequence.

The term "expression cassette": refers to a nucleic acid construct including coding and regulatory sequences operably linked when introduced into a host cell, resulting in the transcription and/or translation of RNA or polypeptide, respectively. An expression cassette is understood to include a promoter allowing the initiation of transcription, the open reading frame of the gene of interest, and a transcription terminator. Generally, the promoter sequence is placed upstream of the gene of interest at a distance compatible with expression control. The "expression cassette" may be a multi-piece nucleic acid construct or a one-piece nucleic acid construct.

The term "open reading frame" (ORF): refers to the normal nucleotide sequence of a structural gene with the potential to encode a protein or polypeptide and begins with a start codon and ends with a stop codon with no stop codon in between to interrupt translation. On an mRNA chain, a ribosome starts translation from the start codon, synthesizes a polypeptide chain along the mRNA sequence, and continues to extend. When a stop codon is encountered, the extension reaction of the polypeptide chain is terminated.

The term "vector": refers to a nucleic acid molecule designed to transport, transfer, and/or store genetic material, as well as to express genetic material and/or integrate genetic material into the chromosomal DNA of a host cell, such as a plasmid vector, a cosmid vector, an artificial chromosome, a phage vector, and other viral vectors. A vector usually consists of at least three basic units, namely a replication source, a selectable marker, and a multiple cloning site.

The term "intron": also known as spacer sequence, refers to a non-coding segment in a gene or mRNA molecule and is an intervening sequence in the DNA of eukaryotic cells. The intronic sequence is transcribed in the mRNA precursor, is removed by splicing, and is ultimately no longer present in the mature mRNA molecule. Depending on whether the splicing process is spontaneous or processed by the spliceosome, introns are divided into self-splicing introns and spliceosomal introns. A self-splicing intron is a special type of intron, a ribozyme that can be cut out by its own action to leave the mRNA. The intron involved in the disclosure is a spliceosomal intron, and the splicing of such an intron requires the help of the spliceosome. There are a splicing donor sequence and a splicing acceptor sequence at both ends of the intron sequence, which are the sequences on both sides of the cutoff and rejoining sites. The spliceosome is a ribonucleoprotein complex dynamically composed of small nuclear RNAs (snRNAs) and protein factors. The spliceosome recognizes the splicing site of the mRNA precursor, catalyzes the splicing reaction, completely cuts out the intron, and then rejoins the upstream and downstream RNA sequences.

The intron mentioned in the disclosure can be a natural intron, or an intron that has been artificially modified and has splicing activity in insect cells, and the source thereof is not limited to insect cells.

The term "AAV serotype": since the discovery of adeno-associated viruses (AAVs), more than 100 AAV serotypes or mutants have been isolated from adenovirus, humans, or primates, and some mammals, among which AAV1-9 is mainly used. The main difference between rAAV vectors of different serotypes is the capsid protein. Different AAV serotypes have certain differences in infection efficiency and tissue specificity.

The genome structures of all known adeno-associated virus serotypes are very similar. AAV is a single-stranded DNA virus with a simple genome structure and a full length of approximately 4.7 kb, as shown in FIG. 1. Its genome contains a rep gene expression cassette, a cap gene expression cassette, and AAV inverted terminal repeats (ITRs) located at both ends of the genome. ITR is a 125-nucleotide palindrome structure at both ends of the genome, can form a self-complementary inverted T-shaped hairpin structure, and is a cis-acting element required for the initiation of DNA replication and packaging of recombinant AAV genome into infectious viral particles. Between the ITR sequences is the virus coding region, where the rep gene expression cassette and the cap gene expression cassette are located.

As a defective virus, AAV cannot replicate independently in the absence of helper viruses. Therefore, AAV can only be integrated into the host cell chromosome at a specific site and remain in a latent state. In the presence of helper virus, the increased expression amount of the rep gene can rescue the AAV genome integrated in the host cell chromosome and replicate AAV DNA in large quantities. The single-stranded rAAV genome is packaged into infectious virus particles under the action of VP capsid protein.

The term "Cap gene": consists of overlapping amino acid sequences encoding the structural VP capsid protein and contains three overlapping open reading frames, encoding three types of subunits: VP1, VP2, and VP3. VP1, VP2, and VP3 contain different start codons and share a stop codon, and VP1 and VP2 share the VP3 sequence. The N-terminus of VP1 has a conserved phospholipase A2 sequence, and this sequence is involved in the escape of the virus from the body and is critical to its infectivity. The VP2 protein is not essential for assembly or infection. The core of the VP3 protein consists of a conserved β-barrel motif, which determines the differences in receptors between different serotypes of AAV and host cells. The correct ratio of the three proteins in wild-type AAV is 6:6:54, which is approximately 1:1:10.

The term "Rep gene": is used to encode four overlapping multifunctional proteins, Rep78, Rep68, Rep52, and Rep40. Rep78 and Rep68 proteins are involved in the replication and integration of AAV and can bind to specific sequences in the ITR. Rep52 and Rep40 proteins have helicase and ATPase activities and participate in single-stranded genome replication and virus assembly. Whether in mammalian cells or insect cells, unspliced mRNA encoding Rep78 and Rep52 proteins is sufficient to prepare rAAV.

The term "relative expression content": is the relative proportion of the expression amounts of different proteins. For instance, an increase in the relative expression content of Rep78/Rep52 protein may mean an increase in Rep78 protein expression amount, or it may mean a decrease in Rep52 protein expression amount.

The term "promoter": is the DNA sequence located upstream of the 5' end of a structural gene and is able to activate RNA polymerase, so that it can accurately bind to the template DNA and have the specificity for transcription initiation.

The term "solid rate": taking the AAV vector as an example, the solid AAV is the AAV vector carrying the target gene. The empty shell AAV vector is an AAV vector that does not carry the target gene, consists of a serotype-specific AAV protein coat, and is usually produced by incomplete viral packaging during the production process. It must be minimized during purification of gene therapy products because these viral capsids do not contain DNA. When they are infused into patients, they compete for the limited number of receptors on the cell surface on the one hand, and they are not beneficial to gene therapy and may cause side effects on the other hand. Further, the increase in empty shell AAV content will lead to an increase in the dosage. The higher the dosage, the higher the risk of serious side effects. The same is true for AAVs that contain incomplete copies of therapeutic genes.

The solid rate refers to the proportion of solid AAV in the prepared AAV vector. The higher the solid rate, the greater the proportion of solid AAV, which proves that the quality of the prepared AAV vector is higher.

The disclosure provides an expression cassette used to express a gene including overlapping open reading frames in a cell, especially in an insect cell, and the expression cassette includes:
  operably linked from a 5' end to a 3' end:
  an artificially constructed sequence; and
  an overlapping open reading frame lacking a first translation initiation codon,
  where the artificially constructed sequence includes a first promoter and a second promoter independent of each other, and a complete sequence of the first translation initiation codon is not included between the first promoter and the second promoter.

In some embodiments, the artificially constructed sequence also includes an intron, and the intron is located between translation initiation codons ATG, for example, between AT and G or between A and TG. The intron is used to form the first translation initiation codon in the artificially constructed sequence through alternative splicing during post-transcriptional processing, so that the overlapping open reading frame can be expressed smoothly.

In some embodiments, the second promoter precedes the first promoter (i.e., precedes the 5' end of the first promoter), and the first promoter precedes the intron. In some other embodiments, the first promoter precedes the intron, and the second promoter is contained within the intron.

In some embodiments, the first promoter is used to express all proteins encoded by the overlapping open reading frame, while the second promoter is used to adjust the relative expression time and relative expression content/expression intensity of these proteins. In some other embodiments, the gene encoded by the expression cassette is a parvovirus Rep gene. The two promoters of the disclosure may be used to adjust the relative expression time and relative expression content/expression intensity of different Rep proteins. Further, a Rep40 protein has a similar function to a Rep52 protein, and a Rep68 protein also has a similar function to a Rep78 protein. Therefore, the first promoter may be used to drive the expression of the Rep68 and/or Rep78 protein(s) and may also be used to drive the expression of the Rep40 protein and/or the Rep52 protein, and the second promoter is used to additionally drive the expression of the Rep40 protein and/or the Rep52 protein.

In some embodiments, the gene encoded by the expression cassette is a parvovirus Cap gene. The two promoters of the disclosure may be used to adjust the relative expression time and relative expression content/expression intensity of different Cap proteins. Further, the first promoter is used to drive the expression of a VP1 protein and may also be used to drive the expression of a VP2/3 protein, and the second promoter is used to additionally drive the expression of the VP2/3 protein.

In some embodiments, the first promoter is active before the second promoter. For instance, the first promoter may be an early and late promoter such as deltaIE1, IE1, 39K, or p6.9, and the second promoter may be a very late promoter such as p10 or polH.

In some other embodiments, the first promoter and the second promoter may produce activity almost simultaneously, for example, the first promoter is p10 and the second promoter is polH.

Since variations in some non-critical sites of the promoters have no impact on their functions, the sequences of the first promoter and the second promoter may also be partially different from the original sequences of the above promoters.

The disclosure further provides an optimized expression cassette for a gene including overlapping open reading frames for use in a cell, especially in an insect cell. The overlapping open reading frames are overlapping open reading frames of a first ORF and a second ORF and include in sequence from a 5' end to a 3' end:
  a first promoter used to drive gene transcription of the first ORF;
  a 5' part of a gene of the first ORF;
  an intron; and
  a 3' part of a gene of the second ORF,
  where the intron includes a second promoter used to drive gene transcription of the second ORF, the first promoter is an immediate early promoter, an early promoter, or a late promoter, the second promoter is a very late promoter, and for example, in some embodiments, the first promoter is deltaIE1, IE1, 39K, or p6.9, and the second promoter is polH or p10.

In some embodiments, the intron is located between any two nucleotides of translation initiation codons ATG of the first ORF. The intron is used to form the first translation initiation codon in the artificially constructed sequence through alternative splicing during post-transcriptional processing.

In some other embodiments, the intron is located between the translation initiation codons ATG of the first ORF and an exon of the first ORF.

In some embodiments, the gene encoded by the expression cassette is a parvovirus Rep gene, the first ORF is used to encode the Rep78 protein, and the second ORF is used to encode the Rep52 protein. The two promoters of the disclosure may be used to adjust the relative expression time and relative expression content/expression intensity of different Rep proteins. Further, the Rep40 protein has a similar function to the Rep52 protein, and the Rep68 protein also has a similar function to the Rep78 protein. Therefore, the first promoter may be used to drive the expression of the Rep68 and/or Rep78 protein(s), and the second promoter is used to drive the expression of the Rep40 protein and/or the Rep52 protein.

In some embodiments, the second promoter contains translation initiation codon and stop codon sequences that are recognized by a ribosome, so that when the intron is not spliced during the post-transcriptional processing of a Rep gene expression cassette driven by the first promoter, the Rep40 protein and/or the Rep52 protein will not be translated and produced. In some embodiments, the gene encoded by the expression cassette is a parvovirus Cap gene. The two promoters of the disclosure may be used to adjust the relative expression time and relative expression content/expression intensity of different Cap proteins. Further, the first promoter is used to drive the expression of the VP1 protein, and the second promoter is used to additionally drive the expression of the VP2 and/or VP3 protein(s).

Since variations in some non-critical sites of the promoters have no impact on their functions, the sequences of the first promoter and the second promoter may also be partially different from the original sequences of the above promoters.

The expression cassette of the Rep gene may be integrated into different baculovirus vectors with the expression cassette of the Cap gene and a sequence of an exogenous gene containing AAV inverted terminal repeats at both ends, or they can be integrated into the same recombinant baculovirus vector. In some embodiments, both the expression cassette of the Rep gene and the expression cassette of the Cap gene can use the abovementioned expression cassette, or one of them can use the abovementioned expression cassette.

In some embodiments, the exogenous gene is a reporter gene and is, for example, a chloramphenicol acetyltransferase encoding gene, a β-galactosidase encoding gene, a β-glucuronidase encoding gene, a *Renilla* luciferase encoding gene, an alkaline phosphatase encoding gene, a firefly luciferase encoding gene, a green fluorescent protein encoding gene, or a red fluorescent protein encoding gene.

In some other embodiments, the exogenous gene is a gene encoding a drug polypeptide, and the drug polypeptide is lipoprotein esterase, apolipoprotein, cytokine, interleukin, or interferon and the like.

In some embodiments, the insect cell is a *Spodoptera frugiperda* cell, a *Trichopodia* cell, a *Drosophila* cell, or a mosquito cell and the like.

Example 1

Figure 2:
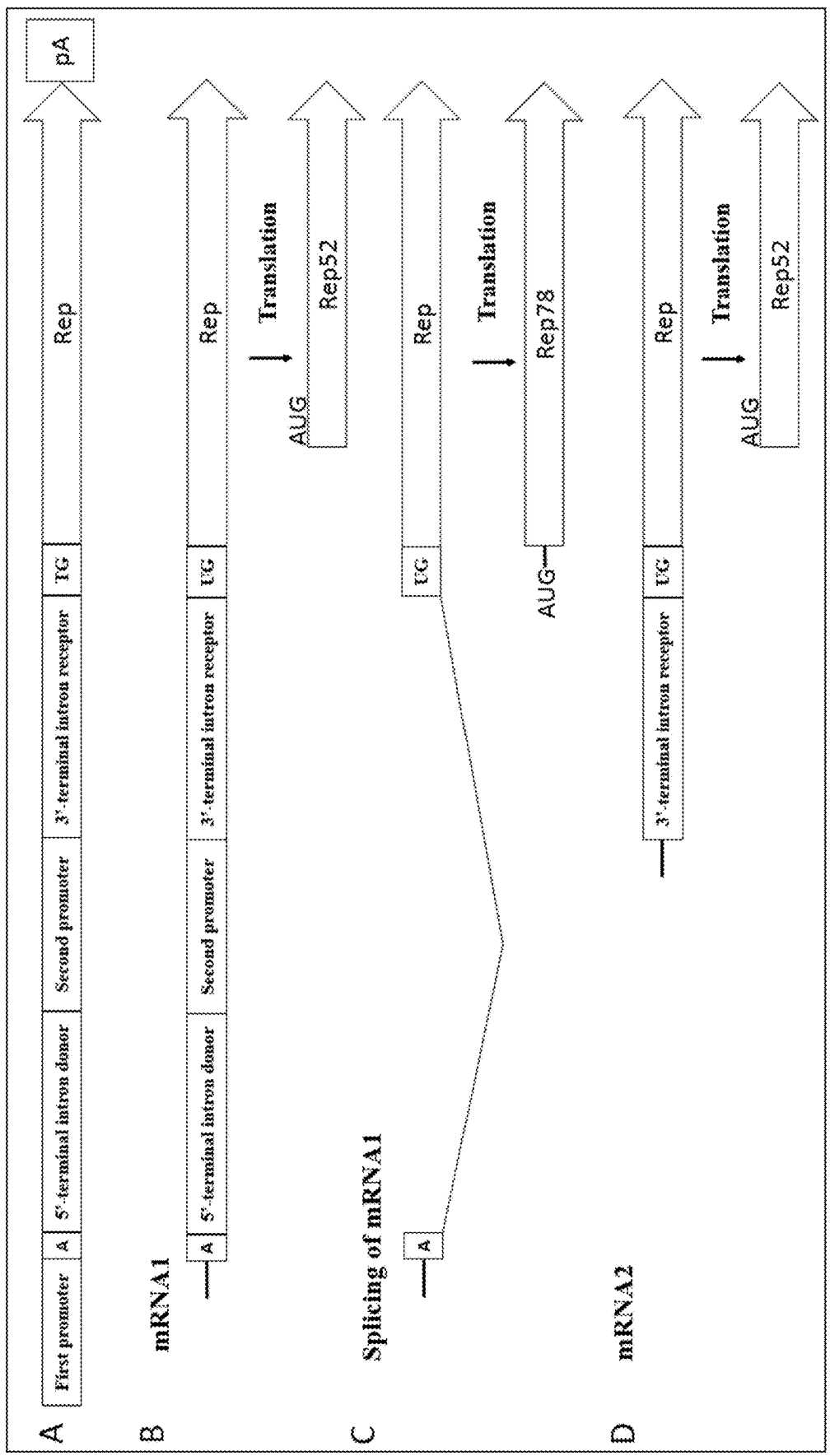
FIG. 2 is a schematic diagram of expression regulation of a RepA-D gene expression cassette I in Examples 1 to 4.

Step One: Construction of Rep Gene Expression Cassette I and Recombinant Baculovirus Vector Containing Rep Gene Expression Cassette I With reference to FIG. 2, herein, content A is a schematic diagram of a DNA chain of the Rep gene expression cassette I, content B is a schematic diagram of the translation and expression of the Rep52 protein when the intron is not spliced during post-transcriptional processing driven by the first promoter, content C is a schematic diagram of the translation and expression of the Rep78 protein after the intron is spliced during post-transcriptional processing driven by the first promoter, and content D is a schematic diagram of the translation and expression of the Rep78 protein after transcription driven by the second promoter. The gene expression cassette, from the 5' end to the 3' end, includes in sequence a first promoter sequence, adenine nucleotide (A), a 5' end donor sequence of the intron, a second promoter sequence, a 3' end acceptor sequence of the intron, thymine nucleotides, guanine nucleotides (TG), and a nucleotide sequence encoding the AAV serotype 2 Rep protein lacking only the translation initiation codons ATG of the Rep78 protein. The overlapping open reading frame nucleotide sequence used to encode the Rep protein is shown in SEQ ID No. 1, its entirety is used to encode the Rep78 protein, and the part used to encode the Rep52 protein is shown in SEQ ID No. 2. There are multiple nucleotide mutations between a Rep78 translation initiation codon and a Rep52 translation initiation codon to eliminate possible translation initiation sites in this region. Herein, deltaIE1 is used as the first promoter sequence and polH is used as the second promoter sequence in this example. The above sequences are connected through artificial direct synthesis or overlap extension PCR amplification to obtain a construct RepA, whose nucleotide sequence is shown in SEQ ID No. 3.

The construct is cloned into a pFastBac vector to prepare a transfer plasmid. The transfer plasmid is transformed into a DH10Bac strain, and a recombinant baculovirus vector AcRepA containing RepA is obtained through the gene transposition reaction mediated by Tn7 transposase.

Step Two: Construction of Cap Gene Expression Cassette

Figure 3:
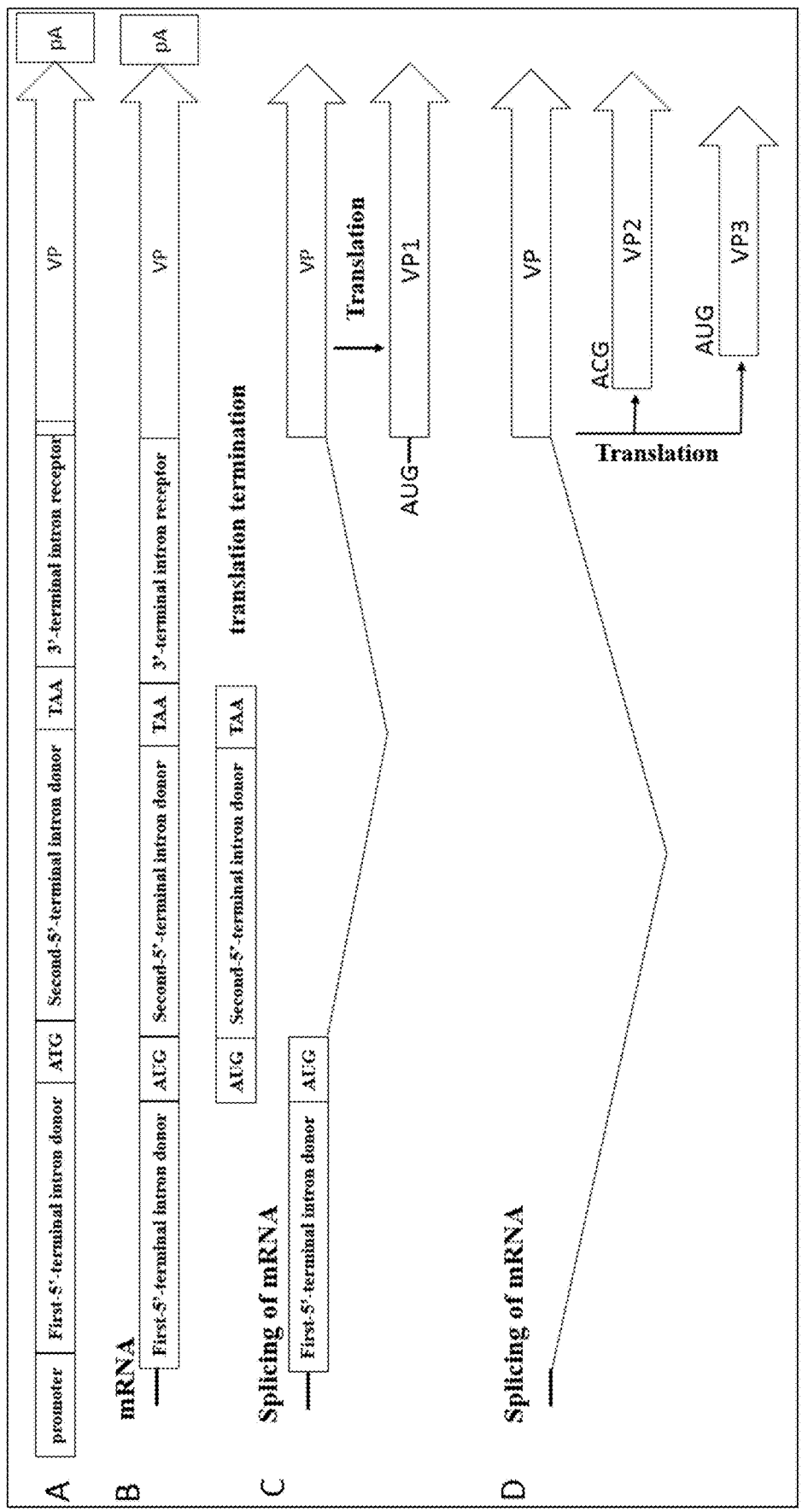
FIG. 3 is a schematic diagram of expression regulation of a Cap gene expression cassette in Example 1.

Construction of a Cap8 expression cassette containing the AAV serotype 8 Cap gene: The Cap gene expression cassette is constructed with reference to the method described in Example 3 of Chinese patent (CN202111105263.5). With reference to FIG. 3, the Cap8 expression cassette, from 5' to 3', includes in sequence, a p10 promoter, an artificially constructed sequence, and a nucleotide sequence encoding the AAV serotype 8 VP protein lacking only the translation initiation codons ATG of the VP1 protein. Herein, the artificially constructed sequence contains the translation initiation codons ATG and contains two intron alternative splicing sites. The amino terminus of the AAV serotype 8 VP protein is encoded with at least one nucleotide mutation to eliminate possible splicing sites within the coding sequence. The above sequences are connected through artificial direct synthesis or overlap extension PCR amplification to obtain a construct Cap8 expression cassette, whose nucleotide sequence is shown in SEQ ID No.4.

Step Three: Construction of Recombinant AAV Bacmid

The method for constructing recombinant AAV bacmid for producing AAV virus in an insect cell is provided with reference to Example 1 in the previously applied patent CN112553257A in this example, and the following steps are included.

(1) A homologous recombination vector containing the essential functional elements Cap and Rep gene expression cassettes of AAV is constructed. The essential functional elements in the homologous recombination vector are then inserted into the C-terminus of the essential gene Ac135 (116492 . . . 117391) in the baculovirus genome in *E. coli* through Red homologous recombination. A recombinant baculovirus vector containing Cap and Rep gene expression cassettes is obtained, numbered Bac-Cap-Rep.

(2) A homologous recombination vector containing an ITR core element (ITR-GOI) is constructed. The ITR core element is numbered I-G-1, and its nucleotide sequence is shown in SEQ ID No. 5. The GOI in the ITR core element uses a red fluorescent protein mcherry gene expression cassette, that is, the miniEfla promoter controls mcherry expression to facilitate detection of rAAV activity in this example.

(3) The shuttle vector constructed in the above step (2) is used to transform competent cells containing the Bac-Cap-Rep recombinant bacmid. The essential functional elements in the homologous recombination vector are then inserted into the C-terminus of the essential gene Ac98 (88502 . . . 88464) in the baculovirus genome in *E. coli* through Red homologous recombination. A recombinant bacmid containing the functional protein components necessary for rAAV production and the ITR core element of the recombinant baculovirus genome is finally obtained, numbered Bac-Cap-Rep-ITR-GOI.

Step Four: Preparation of AAV Recombinant Baculovirus

The recombinant AAV bacmid prepared in step three is transfected into a host cell line and cultured to obtain the AAV recombinant baculovirus, and the specific steps are provided as follows.

The above recombinant bacmid DNA was extracted and transfected into Sf9 insect cells to prepare recombinant baculovirus BEV and rAAV. The transfected Sf9 insect cells successfully produced BEV, and further infection with a large number of replicating and proliferating BEV caused obvious cytopathic effect (CPE) in Sf9 cells. The culture supernatant of Sf9 cells that had undergone CPE was collected, which contained a large amount of BEV, which was the $0^{th}$ generation BEV (P0). At the same time, the Sf9 cells containing a large amount of rAAV were collected. The prepared BEV-P0 was infected into suspension-cultured Sf9 cells at a multiplicity of infection (MOI=1). After 72 hours of infection, the cell activity dropped to less than 50%. The cell culture medium was centrifuged at 1000 g for 5 minutes, and the culture supernatant and cell pellet were collected. The supernatant was labeled as the first generation BEV-P1, and the cells were labeled as rAAV packaged with BEV-P0.

Examples 2 to 4

In Examples 2 to 4, deltaIE1 in Example 1 is replaced with 39K, p6.9, and p10 as the first promoter sequence, and other steps are the same as in Example 1. Constructs RepB, RepC, and RepD, recombinant baculovirus vectors AcRepB, AcRepC, and AcRepD, as well as subsequent recombinant AAV bacmid and AAV recombinant baculovirus are obtained. The nucleotide sequences of RepB-RepD are shown in SEQ ID No. 6-8.

Example 5

Figure 4:
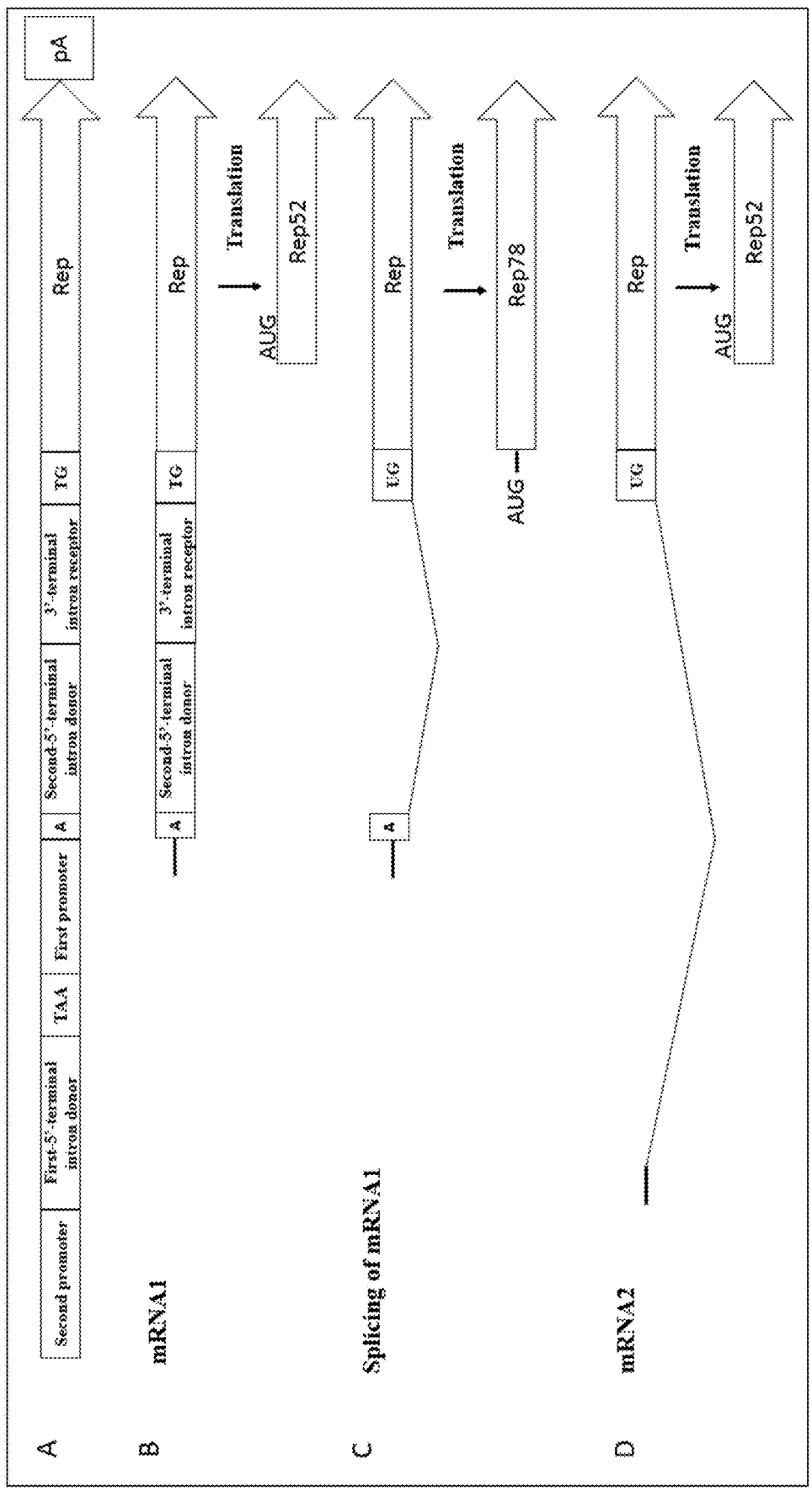
FIG. 4 is a schematic diagram of expression regulation of a RepI-IV gene expression cassette II in Examples 5 to 8.

Step One: Construction of Rep Gene Expression Cassette II and Recombinant Baculovirus Vector Containing Rep Gene Expression Cassette II With reference to what is shown in FIG. 4, herein, content A is a schematic diagram of a DNA chain of the Rep gene expression cassette II, content B is a schematic diagram of the translation and expression of the Rep52 protein when the intron is not spliced during post-transcriptional processing driven by the first promoter, content C is a schematic diagram of the translation and expression of the Rep78 protein after the intron is spliced during post-transcriptional processing driven by the first promoter, and content D is a schematic diagram of the translation and expression of the Rep52 protein after splicing of the first intron splicing donor and splicing acceptor during post-transcriptional processing driven by the second promoter. A TAA translation termination sequence is inserted between the first promoter and the second promoter. During post-transcriptional processing driven by the second promoter, if the intron is not spliced or the second intron splicing donor and splicing acceptor are spliced, protein translation will be terminated prematurely and the Rep78 protein will not be produced. The gene expression cassette, from the 5' end to the 3' end, includes in sequence a second promoter sequence, a 5' end donor sequence of the first intron, a first promoter sequence, adenine nucleotide (A), a 5' end donor sequence of the second intron, a 3' end acceptor sequence of the intron, thymine nucleotides, guanine nucleotides (TG), and a nucleotide sequence encoding the AAV serotype 2 Rep protein lacking only the translation initiation codons ATG of the Rep78 protein. Herein, deltaIE1 is used as the first promoter sequence and polH is used as the second promoter sequence in this example. The above sequences are connected through artificial direct synthesis or overlap extension PCR amplification to obtain a construct RepI, whose nucleotide sequence is shown in SEQ ID No. 9.

The construct was cloned into a pFastBac vector to prepare a transfer plasmid. The transfer plasmid was transformed into a DH10Bac strain, and a recombinant baculovirus vector AcRepI containing RepI was obtained through the gene transposition reaction mediated by Tn7 transposase.

Step two to step four are the same as in Example 1.

Examples 6 to 8

In Examples 6 to 8, deltaIE1 in Example 5 is replaced with 39K, p6.9, and p10 as the first promoter sequence, and other steps are the same as in Example 5. Constructs RepII, RepIII, and RepIV (the nucleotide sequences of which are shown in SEQ ID No. 10-12), recombinant baculovirus vectors AcRepII, AcRepIII, and AcRepIV as well as subsequent recombinant AAV bacmid and AAV recombinant baculovirus are obtained.

Comparative Examples 1 to 4

Figure 5:
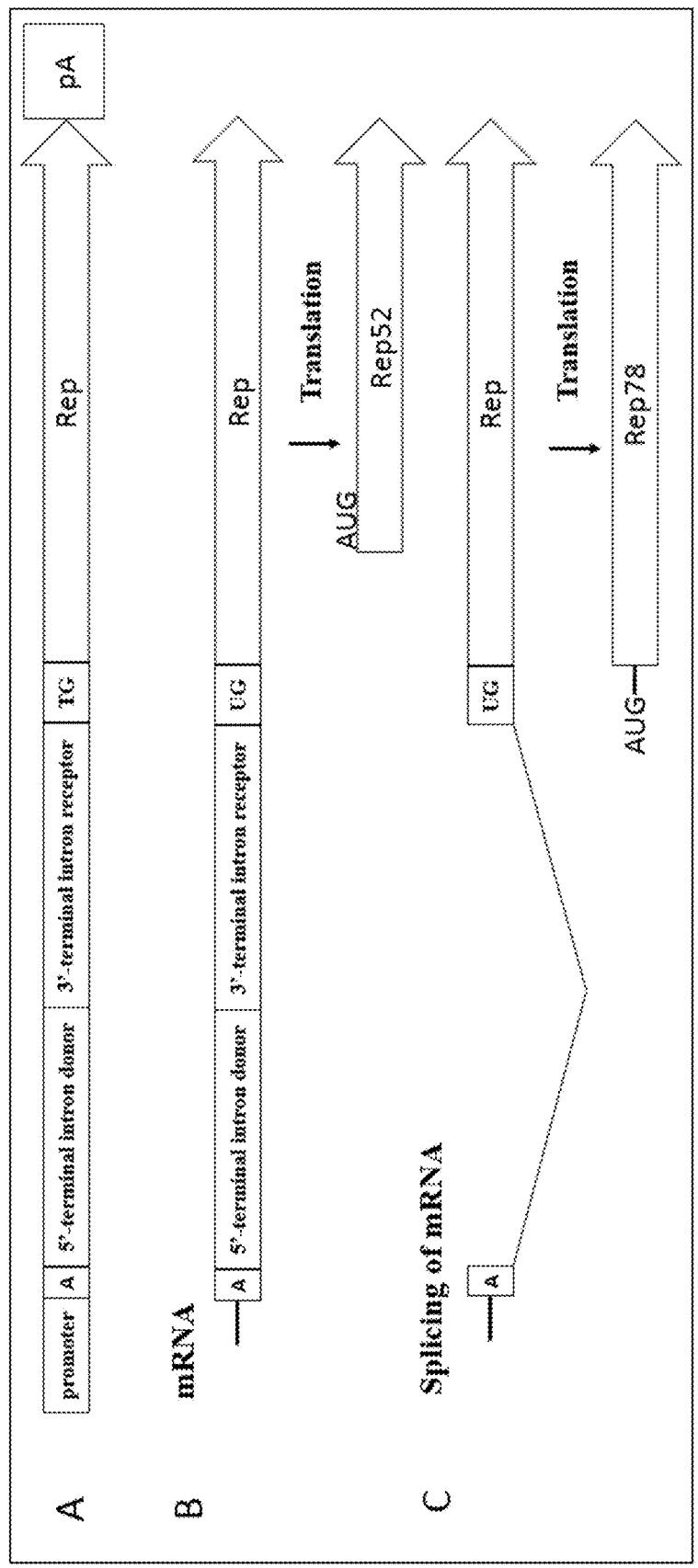
FIG. 5 is a schematic diagram of expression regulation of a Rep1-4 gene expression cassette III in Example 5.

Step one: A Rep gene expression cassette III and a recombinant baculovirus vector containing the Rep gene expression cassette III are constructed, and the Rep gene expression cassette III is constructed with reference to the method described in Example 6 of Chinese patent (CN202111105263.5). With reference to FIG. 5, herein, content A is a schematic diagram of a DNA chain of the Rep gene expression cassette III, content B is a schematic diagram of the translation and expression of the Rep52 protein when the intron is not spliced during post-transcriptional processing, and content C is a schematic diagram of the translation and expression of the Rep78 protein after the intron is spliced during post-transcriptional processing. The gene expression cassette, from the 5' end to the 3' end, includes in sequence a promoter sequence, adenine nucleotide (A), a 5' end donor sequence of the intron, a 3' end acceptor sequence of the intron, thymine nucleotides, guanine nucleotides (TG), and a nucleotide sequence encoding the AAV serotype 2 Rep protein lacking the translation initiation codons ATG of the Rep78 protein. Herein, Comparative Examples 1 to 4 use deltaIE1, 39K, p6.9, and polH as promoter sequences. The above sequences are connected through artificial direct synthesis or overlap extension PCR amplification to obtain the constructs Rep1-4, whose nucleotide sequences are shown in SEQ ID No. 13-16.

The constructs were cloned into a pFastBac vector to prepare a transfer plasmid. The transfer plasmid was transformed into a DH10Bac strain, and recombinant baculovirus vectors AcRep1-4 respectively containing Rep1-4 were obtained through the gene transposition reaction mediated by Tn7 transposase.

Step two to step four are the same as in Example 1.

Experimental Result Verification

For the ease of explanation of the experimental results, the recombinant AAV bacmids (Bac-Cap-Rep-ITR-GOI) constructed according to Examples 1 to 6 and Comparative Example 4 of the disclosure are numbered according to Table 1 according to their corresponding Cap gene expression cassette, Rep gene expression cassette, and ITR core element. The 7 different recombinant AAV bacmids constructed in this example all contain the Cap gene expression cassette, the Rep gene expression cassette, and the ITR core element. Herein, the recombinant AAV bacmid CRI-0 is a control bacmid containing the Rep4 gene expression cassette, and the Rep78/52 protein in the Rep4 gene expression cassette is driven by a single very late strong promoter polH. The details are shown in Table 1.

TABLE 1

List of components of 7 different recombinant AAV bacmids constructed in the Examples and Comparative Examples

| Recombinant AAV bacmid (Bac-Cap-Rep-ITR-GOI) number | Functional protein components and ITR core elements necessary for rAAV production | | |
|---|---|---|---|
| | Cap gene expression cassette | Rep gene expression cassette | ITR core component (ITR-GOI) |
| CRI-0 | Cap8 | Rep4 | I-G-1 |
| CRI-1 | Cap8 | RepA | I-G-1 |
| CRI-2 | Cap8 | RepB | I-G-1 |
| CRI-3 | Cap8 | RepC | I-G-1 |
| CRI-4 | Cap8 | RepD | I-G-1 |
| CRI-5 | Cap8 | RepI | I-G-1 |
| CRI-6 | Cap8 | RepII | I-G-1 |

Verification Example 1 detects the expression of the Rep proteins (Rep78 and Rep52), and the specific steps are as follows.

The above recombinant baculovirus vector DNA was extracted and transfected into Sf9 insect cells to prepare the recombinant baculovirus BEV. The transfected Sf9 insect cells successfully produced BEV, and further infection with a large number of replicating and proliferating BEV caused obvious cytopathic effect (CPE) in Sf9 cells. The culture supernatant of Sf9 cells that had undergone CPE was collected, which contained a large amount of BEV, which was the 0th generation BEV (P0). At the same time, the Sf9 cells containing a large amount of rAAV were collected. The prepared BEV-P0 was infected into suspension-cultured Sf9 cells at a multiplicity of infection (MOI=1). After 72 hours of infection, the cell activity dropped to less than 50%. The cell culture medium was centrifuged at 1000 g for 5 minutes, and the culture supernatant and cell pellet were collected. The supernatant was labeled as the first generation BEV-P1. Continuing to expand the culture, the prepared BEV-P1 was infected into suspension-cultured Sf9 cells at a multiplicity of infection (MOI=1). After 72 hours of infection, the cell activity dropped to less than 50%. The cell culture medium was centrifuged at 1000 g for 5 minutes, and the cell pellet was collected for Western Blot to detect the expression of the Rep proteins (Rep78 and Rep52).

Figure 6:
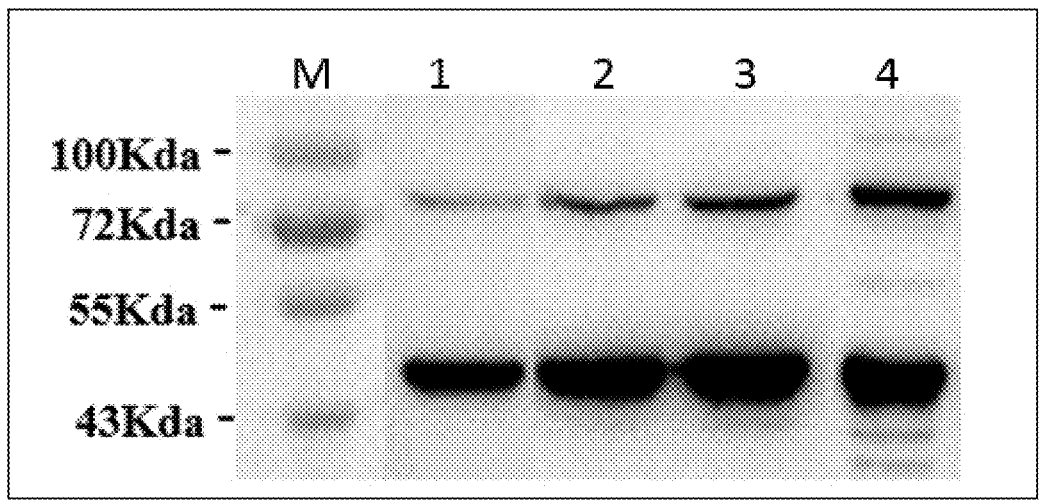
FIG. 6 is a Western Blot detection diagram of a recombinant baculovirus vector AcRepA-D expressing a Rep protein in Examples 1 to 4.
Figure 7:
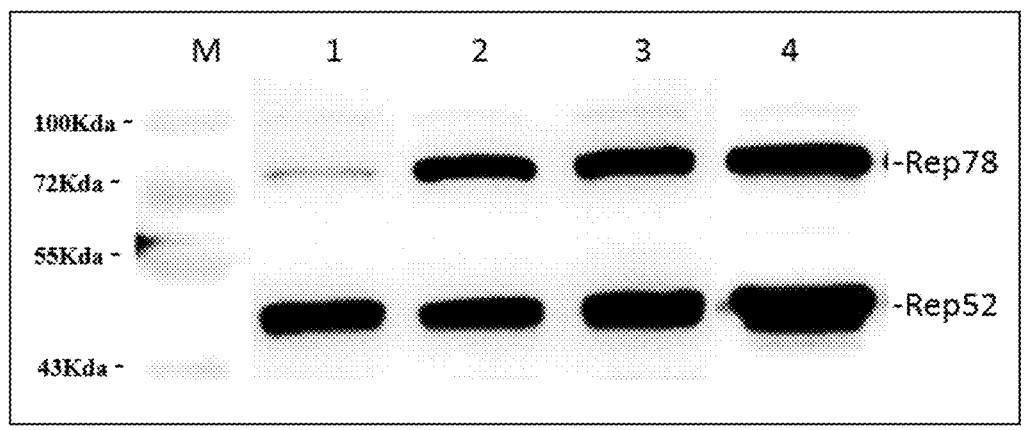
FIG. 7 is a Western Blot detection diagram of a recombinant baculovirus vector AcRepI-IV expressing a Rep protein in Examples 5 to 8.
Figure 8:
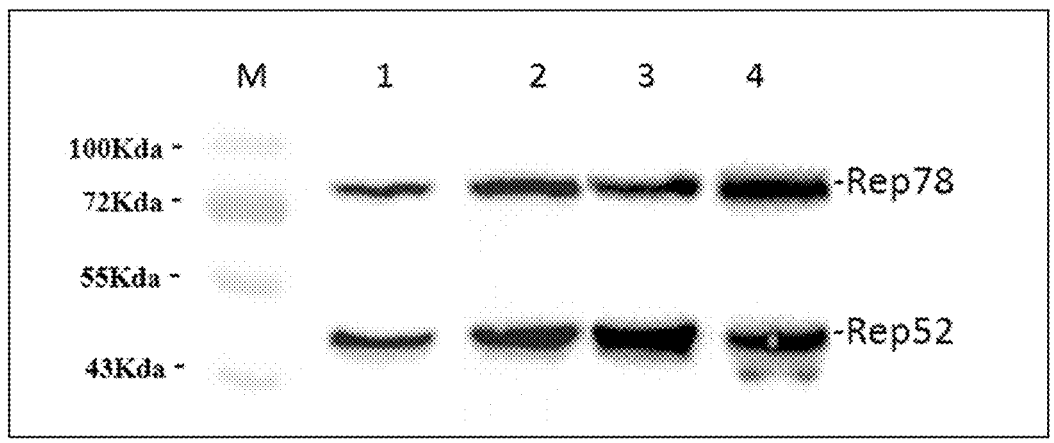
FIG. 8 is a Western Blot detection diagram of a recombinant baculovirus vector AcRep1-4 expressing a Rep protein in Comparative Examples 1 to 4.

FIGS. 6 to 8 are Western Blot detection diagrams of the Rep proteins (Rep78 and Rep52) of the recombinant baculovirus vector containing the Rep gene expression cassette in Examples 1 to 8 and Comparative Examples 1 to 4.

FIG. 6 is a Western Blot detection diagram of the Rep proteins (Rep78 and Rep52) of the recombinant baculovirus vectors AcRepA-D containing the Rep gene expression cassette I, in which lanes 1~4 represent AcRepA-D respectively. It can be seen from FIG. 6 that the above recombinant baculovirus vectors can produce the Rep78 and Rep52 proteins, and the expression amount of the Rep52 protein is significantly higher than that of the Rep78 protein. The high stoichiometric ratio of Rep52 to Rep78 may be a key factor for high rAAV yield. In constructs AcRepA, AcRepB, AcRepC, and AcRepD, the inventors insert the second promoter into the intron sequence to relatively enhance the expression of the Rep52 protein.

FIG. 7 is a Western Blot detection diagram of the Rep proteins (Rep78 and Rep52) of the recombinant baculovirus vectors AcRepI, AcRepII, AcRepIII, and AcRepIV containing the Rep gene expression cassette II, in which lanes 1-4 represent AcRepI-IV respectively. In constructs AcRepI, AcRepII, AcRepIII, and AcRepIV, the inserted second promoter drives the splicing interaction between the first intron splicing donor and the splicing acceptor during post-transcriptional processing to enhance the expression of the Rep52 protein.

FIG. 8 shows the recombinant baculovirus vectors AcRep1-4 containing the Rep gene expression cassette III in Comparative Examples 1-4, in which lanes 1-4 respectively represent the AcRep1-4 in Comparative Examples. It can be seen from the figure that the above recombinant baculovirus vectors can all produce the Rep78 and Rep52 proteins. In constructs AcRep1, AcRep2, AcRep3, and AcRep4, the Rep78/52 protein is expressed through a single promoter. Herein, AcRep1, AcRep2, and AcRep3 use deltaIE1, 39K, and p6.9 promoters to drive the expression of Rep78/52 protein in the immediate early, delayed early, and late stages of baculovirus respectively. Early expression of the Rep78 protein may be beneficial for AAV genome replication and packaging. However, compared with the very late promoter (p10 or polH), the lower promoter strength of deltaIE1, 39K, and p6.9 results in insufficient Rep52 protein, which is not conducive to high rAAV productivity, so it is necessary to enhance the expression of the Rep52 protein.

Verification Example 2 Growth Kinetics Analysis

Figure 9:
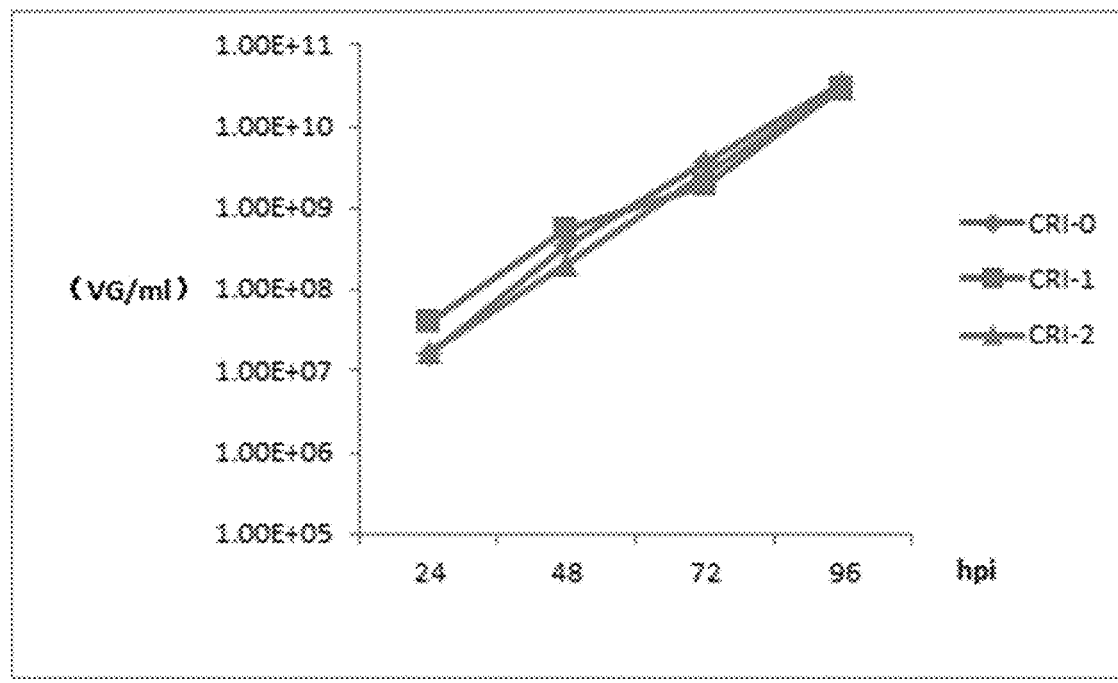
FIG. 9 is a growth kinetic curve of sf9 cells infected with constructs CRI-0, CRI-1, and CRI-2 in Verification Example 1.

The immediate early promoter deltaIE1 is active early in baculovirus infection, and early and abundant expression of the Rep78 protein in insect cells may have a negative impact on the yield of recombinant baculovirus (Urabe et al., 2006, Journal of Virology 80.4:1874-1885). In order to compare the growth kinetics of the recombinant baculoviruses containing different Rep gene expression cassettes in the above Examples and Comparative Examples, the above recombinant baculovirus is used to infect Sf9 cells at a multiplicity of infection (MOI=0.5). The supernatant of the infected cell culture is collected at 24, 48, 72, and 96 hours after infection, and the titer of the second generation BEV-P2 is determined using fluorescence quantitative PCR (qPCR), where the titer unit is expressed in VG/ml (VG, virus genomes). A pair of primers (Q-GP64-F: AACTTGGACAT-TACCCCGCC (SEQ ID NO: 24) and Q-GP64-R: CCGTTGTACGCATACGCCTG (SEQ ID NO: 25)) corresponding to the gp64 gene is used to determine the BEV titer, and titer unit is expressed in VG/ml (VG, virus genomes). The experimental results are shown in FIG. 9. In constructs CRI-0, CRI-1, and CRI-2, the Rep78 protein is expressed in the very late stage, immediate early stage, and delayed early stage respectively. As can be seen from FIG. 9, there are no significant differences in viral titers among CRI-0, CRI-1, and CRI-2, indicating that the early expression of the Rep78 protein in CRI-1 and CRI-2 constructs has less impact on baculovirus replication. In the Rep expression cassette designed by Urabe et al., deltaIE1 alone drives the expression of the Rep78 protein. In CRI-1, the rep gene driven by deltaIE1 promoter is partially transcribed and translated into the Rep78 protein through intron splicing, and partially transcribed and translated into the Rep52 protein, resulting in a relatively lower expression amount of the Rep78 protein, which may be the reason for its reduced impact on baculovirus replication.

Verification Example 3: Purification of Recombinant AAV Virus Particles and Detection of rAAV Virus Titer and Virus Particle Solid Rate This verification example uses Q-PCR to detect the titer of the harvested rAAV virus, and the titer unit is expressed in VG/ml (VG, virus genomes). rAAV titers are measured using a pair of primers (Q-ITR-F: GGAACCCCTAGT-GATGGAGTT (SEQ ID NO: 26) and Q-ITR-R: CGGCCTCAGTGAGCGA (SEQ ID NO: 27)) targeting the ITR sequence. The specific operation is as follows. The culture was continuously expanded according to step four of Example 1 until the Sf9 cells cultured in the suspension were infected with BEV-P2 seed virus according to the multiplicity of infection (MOI=1) for rAAV packaging. The packaging volume is 300 mL to 400 mL. After 3 days of infection, cell activity was monitored. After the activity was lower than 50%, the cell culture was harvested, 500 μl of the harvested mixed solution (mixed solution of cells and supernatant) was put into a 1.5 ml EP tube, frozen and thawed four times in liquid nitrogen, and treated in a 37° C. water bath. 0.1 μl of Benzonase was added to the 500 μl mixed solution, and the mixed solution was mixed in a 37° C. water bath for 1 hour and then in a 95° C. water bath for 10 minutes. Centrifugation was performed at 2500 g for 10 minutes, and the supernatant was collected in a new 1.5 ml EP tube. 200 μl of the supernatant was added to 10 μl of 10% SDS solution to a final concentration of 0.5% SDS. 1.2 μl Proteinase K (working concentration 112 μg/ml) was then added, the final volume was approximately 210 μl, and a 55° C. water bath was performed for 1 hour. After a short centrifugation, a 95° C. water bath was performed for 10 minutes. After mixing, 5 μl of sample was taken out and 145 μl of ddH$_2$O was added to make the final volume 150 μl. After mixing, 10 μl of the sample was taken out and 90 μl of ddH$_2$O was added to make the final volume 100 μl. 2 μl was used as a Q-PCR template to measure the titer of the virus sample. The experimental results are shown in Table 2.

This example uses analytical ultracentrifugation technology (abbreviated as AUC) to detect the solid rate (complete capsid: total capsid) of the recombinant adeno-associated virus (rAAV).

With the use of the sedimentation rate analysis method in the analytical ultracentrifugation technology, the sample is rotated at high speed in the centrifuge, and each component in the sample moves to the bottom of the sample pool. Different components have different movement rates (i.e., sedimentation coefficients) and have different times to fall to the bottom during centrifugation. During this process, the sample distribution state is scanned, and the sedimentation properties of different components are obtained by analyzing its change process over time. The sedimentation coefficient of each component of the sample depends on the molecular weight, molecular shape, and conformation. AUC is generally used to characterize the solid rate of rAAV.

The collected cell culture was purified using an affinity chromatography column (AVIPure AAV8 Resin). 400 μl of the purified rAAV sample was diluted to a dilution factor of OD$_{230}$=0.90, and loaded onto the sample. The sedimentation coefficient and peak area percentage of each peak were recorded. Herein, the sedimentation coefficient of empty shell virus was 55S to 65S, the sedimentation coefficient of solid virus was 80S to 110S, 65S to 80S was the partial part, and greater than 110S was the aggregate. The peaks with sedimentation coefficients between 20S and 150S were normalized to obtain the peak area percentage of each peak, and the empty and solid rate of the virus sample was reported based on the results. The experimental results are shown in Table 2.

TABLE 2

Titer and solid rate detection results of rAAV virions produced using 7 different recombinant AAV bacmids

| Recombinant AAV bacmid number | rAAV virus titer (VG/ml) | rAAV solid rate intact capsids: total capsids |
| --- | --- | --- |
| CRI-0 | 1.12E+12 | 24% |
| CRI-1 | 1.23E+12 | 37% |
| CRI-2 | 1.37E+12 | 45% |
| CRI-3 | 7.37E+11 | 28% |
| CRI-4 | 6.41E+11 | 27% |
| CRI-5 | 1.20E+12 | 32% |
| CRI-6 | 1.27E+12 | 43% |

As can be seen from Table 2, the titers of rAAV virus particles produced using recombinant AAV bacmids CRI-1, CRI-2, CRI-5, and CRI-6 are higher than those of the control bacmid CRI-0, and the solid rate is significantly higher than that of the control bacmid CRI-0. Compared to the control bacmid CRI-0, the early expression of the Rep78 protein and the higher Rep52/Rep78 ratio in bacmids CRI-1, CRI-2, CRI-5, and CRI-6 may be the key factors for their high titers and the high solid rate. The titers of rAAV virus particles produced using the recombinant AAV bacmids CRI-3 and CRI-4 are lower than that of the control bacmid CRI-0, but their solid rates are higher than that of the control bacmid CRI-0. Bacmids CRI-0, CRI-3, and CRI-4 use polH, p6.9, and p10 late promoters respectively to drive the expression of the Rep78 protein, where the polH promoter is the most active. Compared to the control bacmid CRI-0, the lower Rep78 protein expression and higher Rep52/Rep78 ratio in bacmids CRI-3 and CRI-4 may be responsible for their relatively low titers and high solid rates. Increasing the solid rates of viral particles is beneficial to the rAAV product, so fewer particles can be used to obtain a similar amount of genome copies per kilogram, and it is also beneficial to establish a stable downstream purification process.

Example 9

Figure 10:
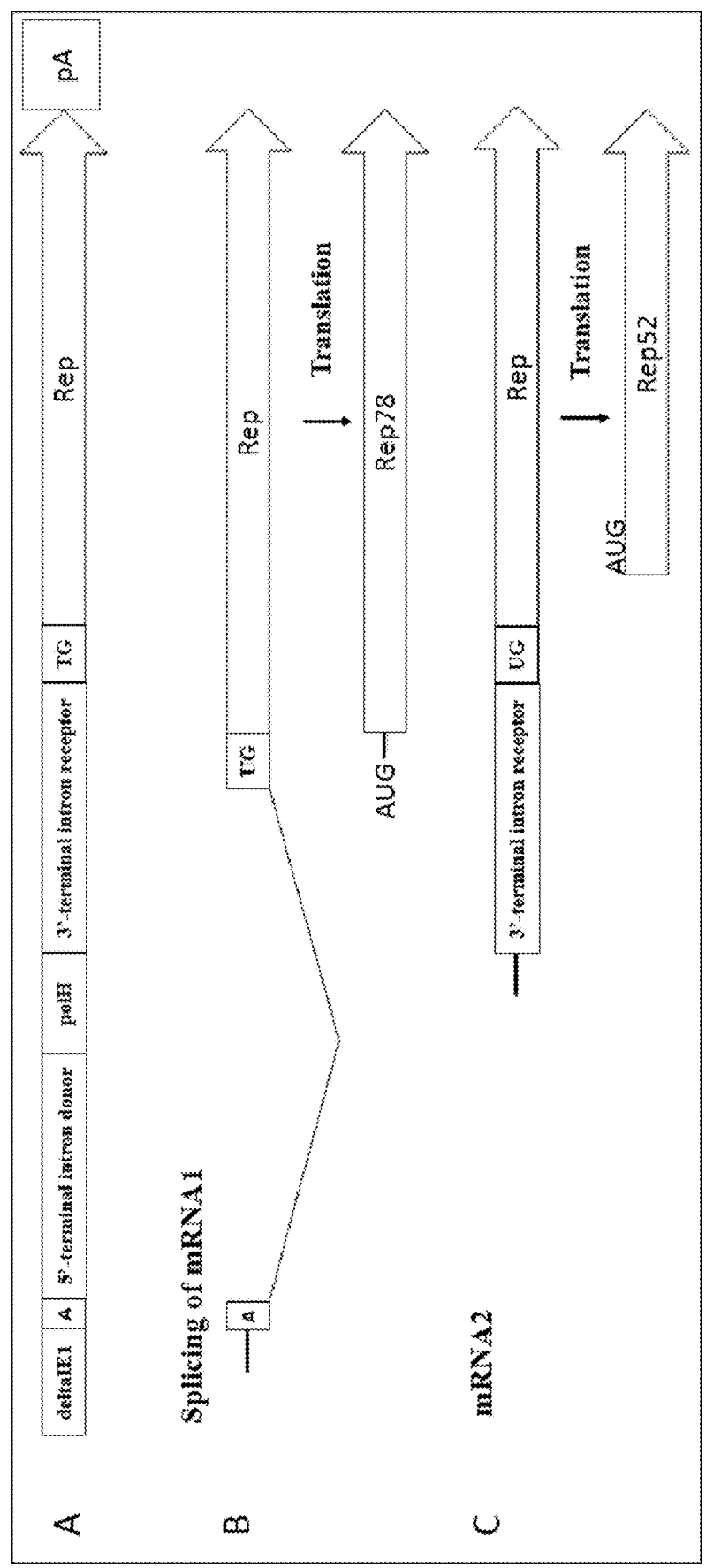
FIG. 10 is a schematic diagram of expression regulation of a RepE gene expression cassette in Example 9.

Step One: Construction of Rep Gene Expression Cassette IV and Recombinant Baculovirus Vector Containing Rep Gene Expression Cassette IV With reference to FIG. 10, herein, content A is a schematic diagram of a DNA chain of the Rep gene expression cassette IV, content B is a schematic diagram of the translation and expression of the Rep78 protein after the intron is spliced during post-transcriptional processing driven by the first promoter, and content C is a schematic diagram of the translation and expression of the Rep78 protein after transcription driven by the second promoter. The gene expression cassette, from the 5' end to the 3' end, includes in sequence a first promoter sequence, adenine nucleotide (A), a 5' end donor sequence of the intron, a second promoter sequence, a 3' end acceptor sequence of the intron, thymine nucleotides, guanine nucleotides (TG), and a nucleotide sequence encoding the AAV serotype 2 Rep protein lacking only the translation initiation codons ATG of the Rep78 protein. The overlapping open reading frame nucleotide sequence used to encode the Rep protein is shown in SEQ ID No. 1, its entirety is used to encode the Rep78 protein, and the part used to encode the Rep52 protein is shown in SEQ ID No. 2. There are multiple nucleotide mutations between a Rep78 translation initiation codon and a Rep52 translation initiation codon to eliminate possible translation initiation sites in this region. In this example, deltaIE1 is used as the first promoter sequence (the nucleotide sequence is shown in SEQ ID No. 17), and polH is used as the second promoter sequence (the nucleotide sequence is shown in SEQ ID No. 18). Herein, the second promoter contains the translation initiation and stop codon sequences that are recognized by a ribosome, so that when the intron is not spliced during the post-transcriptional processing of a Rep gene expression cassette driven by the first promoter, the Rep52 protein will not be translated and produced. The above sequences are connected through artificial direct synthesis or overlap extension PCR amplification to obtain a construct RepE, whose nucleotide sequence is shown in SEQ ID No. 19.

The construct was cloned into a pFastBac vector to prepare a transfer plasmid. The transfer plasmid was transformed into a DH10Bac strain, and a recombinant baculovirus vector AcRepE containing RepE was obtained through the gene transposition reaction mediated by Tn7 transposase.

Step two: Construction of Cap gene expression cassette

This step is the same as step two of Example 1.

Step three: Construction of recombinant AAV bacmid

This step is the same as step three of Example 1.

Step four: Preparation of AAV recombinant baculovirus

This step is the same as step four of Example 1.

Examples 10 to 12

Figure 11:
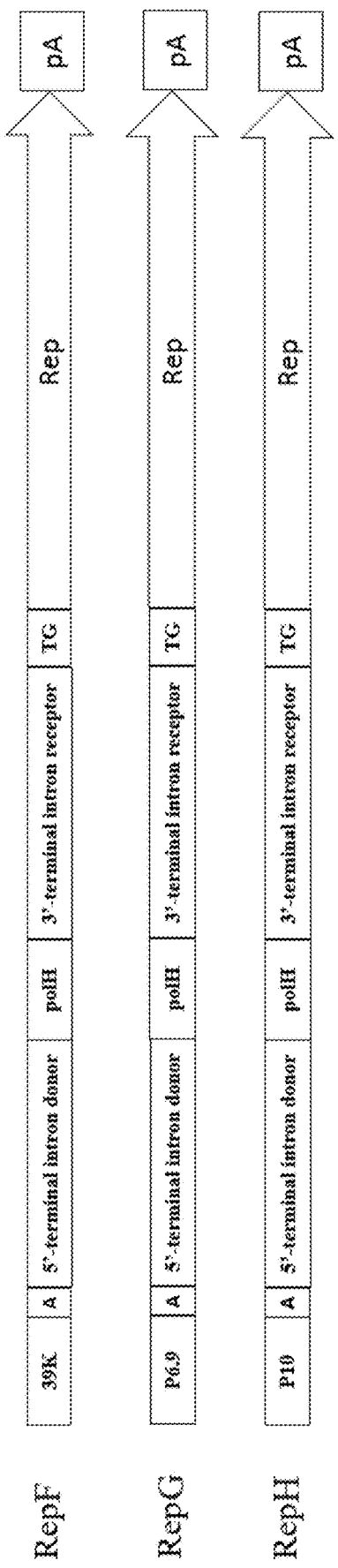
FIG. 11 is a schematic structural diagram of a RepF-H gene expression cassette in Examples 10 to 12.

In Examples 10 to 12, deltaIE1 in Example 9 is replaced with 39K (SEQ ID No. 20), p6.9 (SEQ ID No. 21), and p10 (SEQ ID No. 22) as the first promoter sequence, and other steps are the same as in Example 9. Constructs RepF, RepG, and RepH, as shown in FIG. 11, corresponding recombinant baculovirus vectors AcRepF, AcRepG, and AcRepH, as well as subsequent recombinant AAV bacmid and AAV recombinant baculovirus are obtained.

Comparative Example 5

Step one: A Rep gene expression cassette V and a recombinant baculovirus vector containing the Rep gene expression cassette V are constructed, and the Rep gene expression cassette V is constructed with reference to the method described in Example 6 of Chinese patent (CN202111105263.5). With reference to FIG. 5, herein, content A is a schematic diagram of a DNA chain of the Rep gene expression cassette V, content B is a schematic diagram of the translation and expression of the Rep52 protein when the intron is not spliced during post-transcriptional processing, and content C is a schematic diagram of the translation and expression of the Rep78 protein after the intron is spliced during post-transcriptional processing. The gene expression cassette, from the 5' end to the 3' end, includes in sequence a promoter sequence, adenine nucleotide (A), a 5' end donor sequence of the intron, a 3' end acceptor sequence of the intron, thymine nucleotides, guanine nucleotides (TG), and a nucleotide sequence encoding the AAV serotype 2 Rep protein lacking the translation initiation codons ATG of the Rep78 protein. Herein, Comparative Example 5 uses polH as the promoter sequence. The above sequences are connected through artificial direct synthesis or overlap extension PCR amplification to obtain a construct Rep5, whose nucleotide sequence is shown in SEQ ID No. 23.

The construct was cloned into a pFastBac vector to prepare a transfer plasmid. The transfer plasmid was transformed into a DH10Bac strain, and a recombinant baculovirus vector AcRep5 containing Rep5 was obtained through the gene transposition reaction mediated by Tn7 transposase.

Step two to step four are the same as in Example 9.

Experimental Result Verification

For the ease of explanation of the experimental results, the recombinant AAV bacmids (Bac-Cap-Rep-ITR-GOI) constructed according to Examples 9 to 12 and Comparative Example 5 of the disclosure are numbered according to Table 3 according to their corresponding Cap gene expression cassette, Rep gene expression cassette, and ITR core element. The 5 different recombinant AAV bacmids constructed in this example all contain the Cap gene expression cassette, the Rep gene expression cassette, and the ITR core element. Herein, the recombinant AAV bacmid CRI-7 is a control bacmid containing the Rep5 gene expression cassette, and the Rep78/52 protein in the Rep5 gene expression cassette is driven by a single very late strong promoter polH. The details are shown in Table 3.

TABLE 3

List of components of 7 different recombinant AAV bacmids constructed in the Examples and Comparative Example 5

| Corresponding Example or Comparative Example | Recombinant AAV bacmid (Bac-Cap-Rep-ITR-GOI) number | Functional protein components and ITR core elements necessary for rAAV production | | |
|---|---|---|---|---|
| | | Cap gene expression cassette | Rep gene expression cassette | ITR core component (ITR-GOI) |
| Comparative Example 5 | CRI-7 | Cap8 | Rep5 | I-G-1 |
| Example 9 | CRI-8 | Cap8 | RepE | I-G-1 |
| Example 10 | CRI-9 | Cap8 | RepF | I-G-1 |
| Example 11 | CRI-10 | Cap8 | RepG | I-G-1 |
| Example 12 | CRI-11 | Cap8 | RepH | I-G-1 |

Verification Example 4

The specific steps of the detection of expression of the Rep proteins (Rep78 and Rep52) are as follows.

The above recombinant baculovirus vector DNA was extracted and transfected into Sf9 insect cells to prepare the recombinant baculovirus BEV. The transfected Sf9 insect cells successfully produced BEV, and further infection with a large number of replicating and proliferating BEV caused obvious cytopathic effect (CPE) in Sf9 cells. The culture supernatant of Sf9 cells that had undergone CPE was collected, which contained a large amount of BEV, which was the 0th generation BEV (P0). At the same time, the Sf9 cells containing a large amount of rAAV were collected. The prepared BEV-P0 was infected into suspension-cultured Sf9 cells at a multiplicity of infection (MOI=1). After 72 hours of infection, the cell activity dropped to less than 50%. The cell culture medium was centrifuged at 1000 g for 5 minutes, and the culture supernatant and cell pellet were collected. The supernatant was labeled as the first generation BEV-P1. Continuing to expand the culture, the prepared BEV-PI was infected into suspension-cultured Sf9 cells at a multiplicity of infection (MOI=1). After 72 hours of infection, the cell activity dropped to less than 50%. The cell culture medium was centrifuged at 1000 g for 5 minutes, and the cell pellet was collected for Western Blot to detect the expression of the Rep proteins (Rep78 and Rep52).

Figure 12:
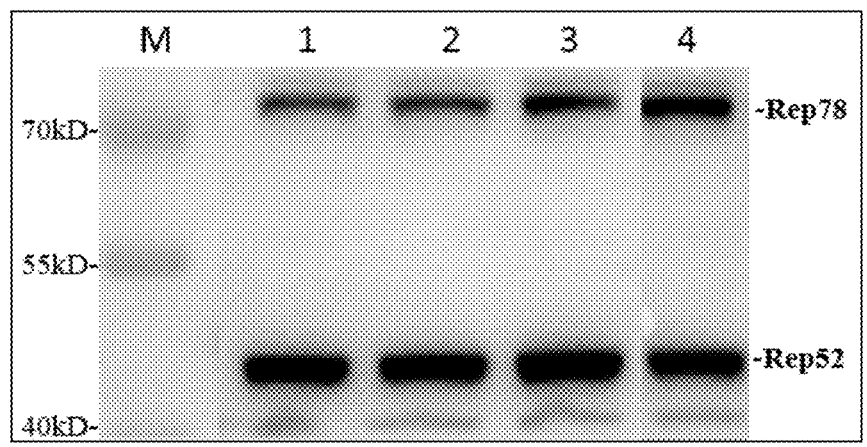
FIG. 12 is a Western Blot detection diagram of a recombinant baculovirus vector AcRepE-H expressing a Rep protein in Examples 9 to 12.
Figure 13:
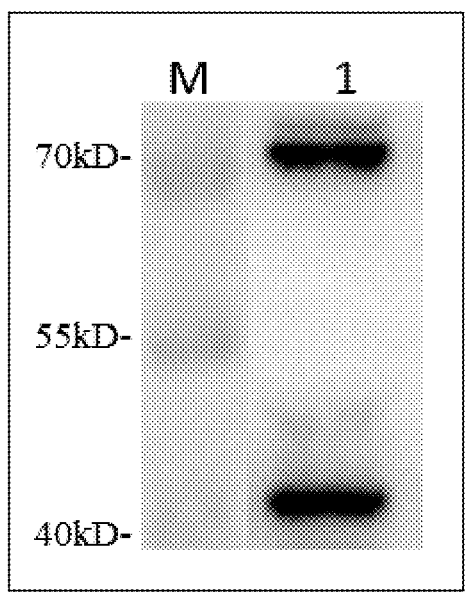
FIG. 13 is a Western Blot detection diagram of a recombinant baculovirus vector AcRep5 expressing a Rep protein in Comparative Example 5.

FIGS. 12 to 13 are Western Blot detection diagrams of the Rep proteins (Rep78 and Rep52) of the recombinant baculovirus vector containing the Rep gene expression cassette in Examples 9 to 12 and Comparative Example 5.

FIG. 12 is a Western Blot detection diagram of the Rep proteins (Rep78 and Rep52) of the recombinant baculovirus vectors AcRepE-H containing the Rep gene expression cassette IV, in which lanes 1-4 represent AcRepE-H respectively. It can be seen from FIG. 12 that the above recombinant baculovirus vectors can produce the Rep78 and Rep52 proteins, and the expression amount of the Rep52 protein of AcRepE-G is significantly higher than that of the Rep78 protein. The high stoichiometric ratio of Rep52 and Rep78 proteins may be a key factor in the high yield of rAAV.

FIG. 13 shows the recombinant baculovirus vector AcRep5 containing the Rep gene expression cassette V in Comparative Example 5, in which lane 1 represents the AcRep5 in Comparative Example 5. It can be seen from the figure that the above recombinant baculovirus vectors can produce the Rep78 and Rep52 proteins.

Verification Example 5

Purification of Recombinant AAV Virus Particles and Detection of Raav Virus Titer and Virus Particle Solid Rate This verification example uses Q-PCR to detect the titer of the harvested rAAV virus, and the titer unit is expressed in VG/ml (VG, virus genomes). rAAV titers are measured using a pair of primers (Q-ITR-F: GGAACCCCTAGT-GATGGAGTT (SEQ ID NO: 26) and Q-ITR-R: CGGCCTCAGTGAGCGA (SEQ ID NO: 27)) targeting the ITR sequence. The specific operation is as follows. The culture was continuously expanded according to step four of Example 9 until the Sf9 cells cultured in the suspension were infected with BEV-P2 seed virus according to the multiplicity of infection (MOI=1) for rAAV packaging. The packaging volume is 300 mL to 400 mL. After 3 days of infection, cell activity was monitored. After the activity was lower than 50%, the cell culture was harvested, 500 µl of the harvested mixed solution (mixed solution of cells and supernatant) was put into a 1.5 ml EP tube, frozen and thawed four times in liquid nitrogen, and treated in a 37° C. water bath. 0.1 µl of Benzonase was added to the 500 µl mixed solution, and the mixed solution was mixed in a 37° C. water bath for 1 hour and then in a 95° C. water bath for 10 minutes. Centrifugation was performed at 2500 g for 10 minutes, and the supernatant was collected in a new 1.5 ml EP tube. 200 µl of the supernatant was added to 10 µl of 10% SDS solution to a final concentration of 0.5% SDS. 1.2 µl Proteinase K (working concentration 112 µg/ml) was then added, the final volume was approximately 210 µl, and a 55° C. water bath was performed for 1 hour. After a short centrifugation, a 95° C. water bath was performed for 10 minutes. After mixing, 5 µl of sample was taken out and 145 µl of ddH$_2$O was added to make the final volume 150 µl. After mixing, 10 µl of the sample was taken out and 90 µl of ddH$_2$O was added to make the final volume 100 µl. 2 µl was used as a Q-PCR template to measure the titer of the virus sample. The experimental results are shown in Table 4.

This example uses a technique of analytical ultracentrifugation (abbreviated as AUC) to detect the solid rate (complete capsid: total capsid) of the recombinant adeno-associated virus (rAAV).

Using the sedimentation rate analysis method in the analytical ultracentrifugation technology, the sample is rotated at high speed in the centrifuge, and each component in the sample moves to the bottom of the sample pool. Different components have different movement rates (i.e., sedimentation coefficients) and have different times to fall to the bottom during centrifugation. During this process, the sample distribution state is scanned, and the sedimentation properties of different components are obtained by analyzing its change process over time. The sedimentation coefficient of each component of the sample depends on the molecular weight, molecular shape, and conformation. AUC is generally used to characterize the solid rate of rAAV.

The collected cell culture was purified using an affinity chromatography column (AVIPure AAV8 Resin). 400 µl of the purified rAAV sample was diluted to a dilution factor of OD$_{230}$=0.90, and loaded onto the sample. The sedimentation coefficient and peak area percentage of each peak were recorded. Herein, the sedimentation coefficient of empty shell virus was 55S to 65S, the sedimentation coefficient of solid virus was 80S to 110S, 65S to 80S was the partial part, and greater than 110S was the aggregate. The peaks with sedimentation coefficients between 20S and 150S were normalized to obtain the peak area percentage of each peak, and the empty and solid rate of the virus sample was reported based on the results. The experimental results are shown in Table 4.

TABLE 4

Titer and solid rate detection results of rAAV virions produced using 5 different recombinant AAV bacmids

| Corresponding Example or Comparative Example | Recombinant bacmid AAV number | rAAV virus titer (VG/ml) | rAAV solid rate (intact capsids: total capsids) |
|---|---|---|---|
| Comparative Example 5 | CRI-7 | 1.12E+12 | 23% |
| Example 9 | CRI-8 | 1.23E+12 | 35% |
| Example 10 | CRI-9 | 1.37E+12 | 39% |
| Example 11 | CRI-10 | 7.37E+11 | 28% |
| Example 12 | CRI-11 | 1.08E+12 | 20% |

As can be seen from Table 4, the titers of rAAV virus particles produced using recombinant AAV bacmids CRI-8 and CRI-9 are higher than those of the control bacmid CRI-7, and the solid rate is significantly higher than that of the control bacmid CRI-7. Compared to the control bacmid CRI-7, the early expression of the Rep78 protein and the higher Rep52/Rep78 ratio in bacmids CRI-8 and CRI-9 may be the key factors for their high titers and the high solid rate. The titer of rAAV virus particles produced using the recombinant AAV bacmid CRI-10 is lower than that of the control bacmid CRI-0, but its solid rate is higher than that of the control bacmid CRI-0. Bacmids CRI-7 and CRI-10 use polH and p6.9 late promoters respectively to drive the expression of the Rep78 protein, where the polH promoter is the most active. Compared to the control bacmid CRI-7, the lower Rep78 protein expression and higher Rep52/Rep78 ratio in the bacmid CRI-10 may be responsible for its relatively low titer and high solid rate. The titer of rAAV virus particles produced using the recombinant AAV bacmid CRI-11 is comparable to that of the control bacmid CRI-0, but its solid rate is slightly lower than that of the control bacmid CRI-7, possibly due to its use of a relatively weak very late promoter to drive Rep78 expression. Increasing the solid rates of viral particles is beneficial to the rAAV product, so fewer particles can be used to obtain a similar amount of genome copies per kilogram, and it is also beneficial to establish a stable downstream purification process.

A person having ordinary skill in the art should be able to easily understand that the above description is only preferred embodiments of the disclosure and is not intended to limit the disclosure. Any modifications, equivalent replacements, and modifications made without departing from the spirit and principles of the disclosure should fall within the protection scope of the disclosure.

The invention claimed is:

1. An expression cassette containing overlapping open reading frames, the overlapping open reading frames being overlapping open reading frames of a first ORF and a second ORF, comprising a second promoter used only to drive gene transcription of the second ORF and further comprising in sequence from a 5' end to a 3' end:
a first promoter at least used to drive gene transcription of the first ORF;
a 5' part of a gene of the first ORF;
an intron; and
a 3' part of a gene of the second ORF,
wherein the second promoter precedes the 5' end of the first promoter or within the intron,
wherein during post-transcriptional processing, the translation initiation codons ATG of the first ORF is formed through alternative splicing of the intron.

2. The expression cassette according to claim 1, wherein the intron is located between any two nucleotides of the translation initiation codons ATG of the first ORF.

3. The expression cassette according to claim 1, wherein the second promoter is within the intron.

4. The expression cassette according to claim 1, wherein the second promoter precedes the 5' end of the first promoter.

5. The expression cassette according to claim 1, wherein the first promoter is only used to drive gene transcription of the first ORF.

6. The expression cassette according to claim 1, wherein the first promoter is used to drive gene transcription of the first ORF and the second ORF.

7. The expression cassette according to claim 1, wherein the gene of the first ORF is used to express a Rep78 and/or Rep68 protein, and the gene of the second ORF is used to express a Rep52 and/or Rep 40 protein.

8. The expression cassette according to claim 1, wherein the gene of the first ORF is used to express a VP1 protein, and the gene of the second ORF is used to express a VP2 and/or VP3 protein(s).

9. The expression cassette according to claim 1, wherein the first promoter is active before the second promoter.

10. The expression cassette according to claim 9, wherein the first promoter is an immediate early promoter, an early promoter, or a late promoter, and the second promoter is a very late promoter.

11. The expression cassette according to claim 1, wherein the first promoter is deltaIE1, IE1, 39K, or p6.9, and the second promoter is polH or p10.

12. The expression cassette according to claim 1, wherein the first promoter is p10, and the second promoter is polH.

13. A nucleic acid molecule, comprising a Cap gene expression cassette and a Rep gene expression cassette, and the Cap gene expression cassette and/or the Rep gene expression cassette is the expression cassette according to claim 1.

14. The nucleic acid molecule according to claim 13, further comprising an exogenous gene.

15. The nucleic acid molecule according to claim 14, wherein AAV inverted terminal repeats are provided at both ends of the exogenous gene.

16. The nucleic acid molecule according to claim 14, wherein the exogenous gene is a reporter gene, and the reporter gene is at least one of a chloramphenicol acetyltransferase encoding gene, a β-galactosidase encoding gene, a β-glucuronidase encoding gene, a *Renilla luciferase* encoding gene, an alkaline phosphatase encoding gene, a firefly luciferase encoding gene, a green fluorescent protein encoding gene, and a red fluorescent protein encoding gene.

17. The nucleic acid molecule according to claim 14, wherein the exogenous gene is a gene encoding a drug polypeptide, and the drug polypeptide is at least one of lipoprotein esterase, apolipoprotein, cytokine, interleukin, and interferon.

18. A recombinant baculovirus vector, comprising the expression cassette according to claim 1.

19. The recombinant baculovirus vector according to claim 18, wherein the recombinant baculovirus vector is an insect cell compatible vector.

20. An isolated insect cell, comprising the recombinant baculovirus vector according to claim 18.

21. The insect cell according to claim 20, wherein the insect cell is a *Spodoptera frugiperda* cell, a *Trichopodia* cell, a *Drosophila* cell, or a mosquito cell.

* * * * *

SEQUENCE LISTING

```
Sequence total quantity: 23
SEQ ID NO: 1              moltype = DNA  length = 1866
FEATURE                   Location/Qualifiers
source                    1..1866
                          mol_type = other DNA
                          note = artificial sequence
                          organism = unidentified
SEQUENCE: 1
atgccgggt  tttacgagat  tgtgattaag  gtccccagcg  accttgacgg  gcatctgccc   60
ggcatttctg  acagctttgt  gaactgggtg  gccgagaagg  agtgggagtt  gccgccagat  120
tctgacttgg  atctgaatct  gattgagcag  gcaccctga   ccgtggccga  gaagctgcag  180
cgcgactttc  tgacggagtg  gcgccgtgtg  agtaaggccc  cggaggccct  tttctttgtg  240
caatttgaga  agggagagag  ctacttccac  ttacacgtgc  tcgtggaaac  caccggggtg  300
aaatccttag  ttttgggacg  tttcctgagt  cagattcgcg  aaaaactgat  tcagagaatt  360
taccgcggga  tcgagccgac  tttgccaaac  tggttcgcgg  tcacaaagac  cagaaaccgc  420
gccggaggcg  ggaacaaggt  ggtggacgag  tgctacatcc  ccaattactt  gctccccaaa  480
acccagcctg  agctccagtg  ggcgtggact  aatttagaac  agtatttaag  cgcctgtttg  540
aatctcacgg  agcgtaaacg  gttggtggcg  cagcatctga  cgcacgtgtc  gcagacgcag  600
gagcagaaca  aagagaatca  gaatcccaat  tctgacgcgc  cggtgatcag  atcaaaaact  660
tcagccaggt  acatggagct  ggtcgggtgg  ctcgtggaca  aggggattac  ctcggagaag  720
cagtggatcc  aggaggacca  ggcctcatac  atctccttca  atgcggcctc  caactcgcgg  780
tcccaaatca  aggctgcctt  ggacaatgcg  ggaaagatta  tgagcctgac  taaaaccgcc  840
cccgactacc  tggtgggcca  gcagcccgtg  gaggacattt  ccagcaatcg  gatttataaa  900
attttggaac  taaacgggta  cgatcccaa   tatgcggctt  ccgtctttct  gggatgggcc  960
acgaaaaagt  tcggcaagag  gaacaccatc  tggctgtttg  ggcctgcaac  taccgggaag 1020
accaacatcg  cggaggccat  agcccacact  gtgcccttct  acgggtgcgt  aaactggacc 1080
aatgagaact  ttcccttcaa  cgactgtgtc  gacaagatgg  tgatctggtg  ggaggagggg 1140
aagatgaccg  ccaaggtcgt  ggagtcggcc  aaagccattc  tcggaggaag  caagtgcgc  1200
gtggaccaga  aatgcaagtc  ctcggcccag  atagaccga   ctcccgtgat  cgtcacctcc 1260
aacaccaaca  tgtgcgccgt  gattgacggg  aactcaacga  ccttcgaaca  ccagcagccg 1320
ttgcaagacc  ggatgttcaa  atttgaactc  acccgccgtc  tggatcatga  ctttgggaag 1380
gtcaccaagc  aggaagtcaa  agacttttc   cggtgggcaa  aggatcacgt  ggtttgaggtg 1440
gagcatgaat  tctacgtcaa  aaagggtgga  gccaagaaaa  gacccgcccc  cagtgacgca 1500
gatataagtg  agcccaaacg  ggtgcgcgag  tcagttgcgc  agccatcgac  gtcagacgcg 1560
gaagcttcga  tcaactacgc  agacaggtac  caaaacaaat  gttctcgtca  cgtgggcatg 1620
aatctgatgc  tgtttccctg  cagacaatgc  gagagaatga  atcagaattc  aaatatctgc 1680
ttcactcacg  gacagaaaga  ctgtttagag  tgctttcccg  tgtcagaatc  tcaacccgtt 1740
tctgtcgtca  aaaggcgta   tcagaaactg  tgctacattc  atcatatcat  gggaaaggtg 1800
ccagacgctt  gcactgcctg  cgatctggtc  aatgtggatt  tggatgactg  catctttgaa 1860
caataa                                                                1866

SEQ ID NO: 2              moltype = DNA  length = 1194
FEATURE                   Location/Qualifiers
```

```
source                  1..1194
                        mol_type = other DNA
                        note = artificial sequence
                        organism = unidentified
SEQUENCE: 2
atggagctgg tcgggtggct cgtggacaag gggattacct cggagaagca gtggatccag   60
gaggaccagg cctcatacat ctccttcaat gcggcctcca actcgcggtc ccaaatcaag  120
gctgccttgg acaatgcggg aaagattatg agcctgacta aaaccgcccc cgactacctg  180
gtgggccagc agcccgtgga ggacatttcc agcaatcgga tttataaaat tttggaacta  240
aacgggtacg atccccaata tgcggcttcc gtctttctgg atgggccac gaaaaagttc  300
ggcaagagga acaccatctg gctgtttggg cctgcaacta ccgggaagac caacatcgcg  360
gaggccatag cccacactgt gcccttctac ggtgcgtaa actggaccaa tgagaacttt  420
cccttcaacg actgtgtcga caagatggtg atctggtggg aggaggggaa gatgaccgcc  480
aaggtcgtgg agtcggccaa agccattctc ggaggaagca aggtgcgcgt ggaccagaa   540
tgcaagtcct cggcccagat agacccgact cccgtgatcg tcacctccaa caccaacatg  600
tgcgccgtga ttgacgggaa ctcaacgacc ttcgaacacc agcagccgtt gcaagaccgg  660
atgttcaaat ttgaactcac ccgccgtctg gatcatgact ttgggaaggt caccaagcag  720
gaagtcaaag acttttttccg gtgggcaaag gatcacgtgg ttgaggtgga gcatgaattc  780
tacgtcaaaa agggtggagc caagaaaaga cccgccccca gtgacgcaga tataagtgag  840
cccaaacggg tgcgcgagtc agttgcgcag ccatcgacgt cagacgcgga agcttcgatc  900
aactacgcag acaggtacca aaacaaatgt tctcgtcacg tgggcatgaa tctgatgctg  960
tttccctgca gacaatgcga gagaatgaat cagaattcaa atatctgctt cactcacgga 1020
cagaaagact gtttagagtg cttttcccgt gtcagaatctc aacccgtttc tgtcgtcaaa 1080
aaggcgtatc agaaactgtg ctacattcat catatcatgg gaaaggtgcc agacgcttgc 1140
actgccgcg atctggtcaa tgtggatttg gatgactgca tctttgaaca ataa         1194

SEQ ID NO: 3       moltype = DNA    length = 2222
FEATURE            Location/Qualifiers
source             1..2222
                   mol_type = other DNA
                   note = artificial sequence
                   organism = unidentified
SEQUENCE: 3
aataaacgat aacgccgttg gtggcgtgag gcatgtaaaa ggttacatca ttatcttgtt   60
cgccatccgg ttggtataaa tagacgttca tgttggtttt tgtttcagtt gcaagttggc  120
tgcggcgcgc gcagcacctt tgcgggatcc tcaggtagta agtattcatt gtaaatctga  180
tattattgt attattatac ctacctaatt tgcagtgcag atcattgaga taattaaaat   240
tataaccatc tcgcaaataa ataagtattt tactgttttc gtaacagttt tgtaataaaa  300
aaacctataa atcccattac ggcagtataa attcgttcat tttggatatt gtttcagtgc  360
cggggtttta cgagattgtg attaaggtcc ccagcgacct tgacgggcat ctgcccggca  420
tttctgacag ctttgtgaac tgggtggccg agaaggagtg ggagttgccg ccagattctg  480
acttggatct gaatctgatt gagcaggcac ccctgaccgt ggccgagaag ctgcagcgcg  540
actttctgac ggagtggcgc cgtgtgagta aggccccgga ggcccttttc tttgtgcaat  600
ttgagaaggg agagagctac ttccacttac acgtgctcgt ggaaaccacc ggggtgaaat  660
ccttagtttt gggacgtttc ctgagtcaga ttcgcgaaaa actgattcag agaatttacc  720
gcgggatcga gccgactttg ccaaactggt tcgcggtcac aaagaccaga aacggcgccg  780
gaggcgggaa caaggtggtg gacgagtgct acatccccaa ttacttgctc cccaaaaccc  840
agcctgagct ccagtgggcg tggactaatt tagaacagta tttaagcgcc tgtttgaatc  900
tcacggagcg taaacggttg gtggcgcagc atctgacgca cgtgtcgcag acgcaggagc  960
agaacaaaga gaatcagaat cccaattctg acgcgccggt gatcagatca aaaacttcag 1020
ccaggtacat ggagctggtc gggtggctgg tggacaaggg gattacctcg gagaagcat  1080
ggatccagga ggaccaggcc tcatacatct ccttcaatgc ggcctccaac tcgcggtccc 1140
aaatcaaggc tgccttggac aatgcgggaa agattatgag cctgactaaa ccgcccccg  1200
actacctggt gggccagcag cccgtggagg acatttccag caatcggatt tataaaattt 1260
tggaactaaa cgggtacgat cccaatatgc ggcttccgt cttttctggga tgggccacga 1320
aaaagttcgg caagaggaac accatctggc tgtttgggcc tgcaactacc gggaagacca 1380
acatcgcgga ggccatagcc cacactgtgc ccttctacgg tgcgtaaac tggaccaatg  1440
agaactttcc cttcaacgac tgtgtcgaca agatggtgat ctggtgggag gaggggaaga 1500
tgaccgccaa ggtcgtggag tcggccaaag ccattctcgg aggaagcaag gtgcgcgtgg 1560
accagaaatg caagtcctcg gcccagatag acccgactcc cgtgatcgtc acctccaaca 1620
ccaacatgtg cgccgtgatt gacgggaact caacgacctt cgaacaccag cagccgttgc 1680
aagaccggat gttcaaattt gaactcaccc gccgtctgga tcatgacttt gggaaggtca 1740
ccaagcagga agtcaaagac ttttttccggt gggcaaagga tcacgtggtt gaggtggagc 1800
atgaattcta cgtcaaaaag ggtggagcca agaaaagacc cgccccagt gacgcagata  1860
taagtgagcc caaacgggtg cgcgagtcag ttgcgcagcc atcgacgtca gacgcggaag 1920
cttcgatcaa ctacgcagac aggtaccaaa acaaatgttc tcgtcacgtg ggcatgaatc 1980
tgatgctgtt tccctgcaga caatgcgaga gaatgaatca gaattcaaat atctgcttca 2040
ctcacggaca gaaagactgt ttagagtgct tttcccgtgtc agaatctcaa cccgtttctg 2100
tcgtcaaaaa ggcgtatcag aaactgtgct acattcatca tatcatggga aaggtgccag 2160
acgcttgcac tgcctgcgat ctggtcaatg tggatttgga tgactgcatc tttgaacaat 2220
aa                                                                 2222

SEQ ID NO: 4       moltype = DNA    length = 2583
FEATURE            Location/Qualifiers
source             1..2583
                   mol_type = other DNA
                   note = artificial sequence
                   organism = unidentified
SEQUENCE: 4
```

```
gacctttaat tcaacccaac acaatatatt atagttaaat aagaattatt atcaaatcat    60
ttgtatatta attaaaatac tatactgtaa attacatttt atttacaatc actcgacgaa   120
gacttgatca cccggggggac aaggtaagta ttcattgtaa atctgatatt atttgtatta   180
ttatacctac ctaatttgca gtgcaggccg ccatggtaag tatcgataac tttgttttct   240
ttcacattta caactccgac atacaaattg taatttatt actgttttggt ccataaacac    300
ttgtttacca tttcctttt tacaagtttt aatattttct gcatatataa aacattattt   360
attttgcagg ctgccgacgg ttatctaccc gattggctcg aggacaacct ctctgagggc   420
attcgcgagt ggtgggcgct gaaacctgga gccccgaagc ccaaagccaa ccagcaaaag   480
caggacgacg gccggggtct ggtgcttcct ggctacaagt acctcggacc cttcaacgga   540
ctcgacaagg gggagcccgt caacgcggcg gacgcagcgg ccctcgagca cgacaaggcc   600
tacgaccagc agctgcaggc gggtgacaat ccgtacctgc ggtataacca cgccgacgcc   660
gagtttcagg agcgtctgca agaagatacg tcttttgggg caacctcgg gcgagcagtc   720
ttccaggcca agaagcgggt tctcgaacct ctcggtctgg ttgaggaagg cgctaagacg   780
gctcctggaa agaagagacc ggtagagcca tcacccccagc gttctccaga ctcctctacg   840
ggcatcggca agaaaggcca acagcccgcc agaaaaagac tcaattttgg tcagactggc   900
gactcagagt cagttccaga ccctcaacct ctcggagaac ctccagcagc gccctctggt   960
gtgggaccta atacaatggc tgcaggcggt ggcgcaccaa tggcagacaa taacgaaggc  1020
gccgacggag tgggtagttc ctcgggaaat tggcattgcg attccacatg gctgggcgac  1080
agagtcatca ccaccagcac ccgaacctgg gccctgccca cctacaacaa ccacctctac  1140
aagcaaatct ccaacgggac atcgggagga gccaccaacg acaacaccta cttcggctac  1200
agcacccct ggggggtattt tgactttaac agattccact gccactttc accacgtgac  1260
tggcacggac tcatcaacaa caactgggga ttccggcaga agactcag cttcaagctc  1320
ttcaacatcc aggtcaagga ggtcacgcag aatgaaggca ccaagaccat cgccaataac  1380
ctcaccagca ccatccaggt gtttacggac tcggagtacc agctgccgta cgttctcggc  1440
tctgcccacc agggctgcct gcctccgttc ccggcggacg tgttcatgat tccccagtac  1500
ggctacctaa cactcaacaa cggtagtcag ccgtgtcag gctcctcctt ctactgcctg  1560
gaatactttc cttcgcagat gctgagaacc ggcaacaact tccagtttac ttacaccttc  1620
gaggacgtgc ctttccacag cagctacgcc cacagccaga gcttggaccg gctgatgaat  1680
cctctgattg accagtacct gtactacttg tctcggactc aaacaacagg aggcacggca  1740
aatacgacaga ctctgggctt cagccaaggt gggcctaata caatgccaa tcaggcaaag  1800
aactggctgc caggaccctg ttaccgccaa caacgcgtct caacgacaac cgggcaaaac  1860
aacaatagca actttgcctg gactgctggg accaaaatacc atctgaatgg aagaaattca  1920
ttggctaatc ctggcatcgc tatggcaaca cacaaagacg acgaggagcg ttttttttccc  1980
agtaacggga tcctgatttt tggcaaacaa aatgctgacaa gagacaatgc ggattacagc  2040
gatgtcatgc tcaccagcga ggaagaaatc aaaaccacta accctgtggc tacagaggaa  2100
tacggtatcg tggcagataa cttgcagcag caaaacacgg ctcctcaaat tggaactgtc  2160
aacagccagg gggccttacc cggtatggtc tggcagaacc gggacgtgta cctgcagggt  2220
cccatctggg ccaagattcc tcacacggac ggcaacttcc acccgtctcc gctgatgggc  2280
ggctttggcc tgaaacatcc tccgcctcag atcctgatca agaacacgcc tgtacctgcg  2340
gatcctccga ccaccttcaa ccagtcaaag ctgaactctt tcatcacgca atacagcacc  2400
ggacaggtca gcgtggaaat tgaatgggag ctgcagaagg aaaacagcaa gcgctggaac  2460
cccgagatcc agtacacctc caactactac aaatctacaa gtgtggactt tgctgttaat  2520
acagaaggcg tgtactctga accccgcccc attggcaccc gttacctcac ccgtaatctg  2580
taa                                                                 2583
SEQ ID NO: 5           moltype = DNA   length = 2407
FEATURE                Location/Qualifiers
source                 1..2407
                       mol_type = other DNA
                       note = artificial sequence
                       organism = unidentified
SEQUENCE: 5
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccgca cgcgccgcc gtcagtgggc agagcgcaca   180
tcgcccacag tccccgagaa gttggggga ggggtcggca attgaaccgg tgcctagaga   240
aggtggcgcg gggtaaactg gaaagtgat gtcgtgtact ggctccgcct tttcccgag    300
ggtgggggag aaccgtatat aagtgcagta gtcgccgtga acgttcttt cgcaacggg    360
tttgccgcca gaacacgcgt aagggatccg ccaccatggt gagcaagggc gaggaggata   420
acatggccat catcaaggag ttcatgcgct tcaaggtgca catggagggc tccgtgaacg   480
gccacgagtt cgagatcgag ggcgagggcg agggccgccc ctacgagggc acccagaccg   540
ccaagctgaa ggtgaccaag ggtggccccc tgcccttcgc ctgggacatc ctgtcccctc   600
agttcatgta cggctccaag gcctacgtga agcaccccgc cgacatcccc gactacttga   660
agctgtcctt ccccgagggc ttcaagtggg agcgcgtgat gaacttcgag gacggcggtc   720
tggtgaccgt gacccaggac tcctccctgc aggacggcga gttcatctac aaggtgaagc   780
tgcgcggcac caacttcccc tccgacggcc ccgtaatgca gaagaagacc atgggctggg   840
aggcctcctg cgagcggatg taccccgagg acggcgccct gaagggcgag atcaagcaga   900
ggctgaagct gaaggacggc ggccactacg acgctgaggt caagaccacc tacaaggcca   960
agaagcccgt gcagctgccc ggcctacaa cgtcaacat caagttggac atcacctccc  1020
acaacgagga ctacaccatc gtgaacagt acgaacgcgc cgaggccgc cactccaccg  1080
gcggcatgga cgagctgtac aagtaagaat tcgatatcaa gcttatcgat aatcaacctc  1140
tggattacaa aatttgtgaa agattgactg gtattcttaa ctatgttgct ccttttacgc  1200
tatgtggata cgctgcttta atgcctttgt atcatgctat tgcttccccgt atggctttca  1260
ttttctcctc cttgtataaa tcctggttgc tgtctcttta tgaggagttg tggccccgttg  1320
tcaggcaacg tggcgtggtg tgcactgtgt ttgctgacgc aacccccact ggttggggca  1380
ttgccaccac ctgtcagctc ctttccggga ctttcgcttt ccccctccct attgccacgg  1440
cggaactcat cgccgcctgc cttgcccgct gctggacagg gctcggctg ttgggcactg  1500
acaattccgt ggtgttgtcg gggaaatcat cgtccttcc ttggctgctc gcctgtgttg  1560
ccacctggat tctgcgcggg acgtccttct gctacgtccc ttcggccctc aatccagcgg  1620
```

```
accttccttc ccgcggcctg ctgccggctc tgcggcctct tccgcgtctt cgccttcgcc   1680
ctcagacgag tcggatctcc ctttgggccg cctcccgca tcgataccga gcgctgctcg   1740
agagatctac gggtggcatc cctgtgaccc ctccccagtg cctctcctgg ccctggaagt   1800
tgccactcca gtgcccacca gccttgtcct aataaaatta agttgcatca ttttgtctga   1860
ctaggtgtcc ttctataata ttatggggtg gagggggctg gtatggagca aggggcaagt   1920
tgggaagaca acctgtaggg cctgcgggt ctattgggaa ccaagctgga gtgcagtggc   1980
acaatcttgg ctcactgcaa tctccgcctc ctgggttcaa gcgattctcc tgcctcagcc   2040
tcccgagttg ttgggattcc aggcatgcat gaccaggctc agctaatttt tgtttttttg   2100
gtagagacag ggtttcacca tattggccag gctggtctcc aactcctaat ctcaggtgat   2160
ctacccacct tggcctccca aattgctggg attacaggcg tgaaccactg ctcccttccc   2220
tgtccttctg attttgtagg taaccacgtg cggaccgagc ggccgcagga acccctagtg   2280
atggagttgg ccactccctc tctgcgcgct cgctcgctca ctgaggccgg gcgaccaaag   2340
gtcgcccgac gcccgggctt tgcccgggcg gcctcagtga gcgagcgagc gcgcagctgc   2400
ctgcagg                                                            2407
SEQ ID NO: 6         moltype = DNA length = 2406
FEATURE              Location/Qualifiers
source               1..2406
                     mol_type = other DNA
                     note = artificial sequence
                     organism = unidentified
SEQUENCE: 6
cacatgttgg acatcgtgtc gtttgagcgt ataaaagaat atataagagc taatttaggc     60
catttcacag taatcaccga caaatgttcg aagcgtaagg tgtgtcttca tcacaaacga    120
attgccaggt tgttgggcat taaaaaaata tatcatcaag aatacaaacg ggttgtttca    180
aaggtttaca agaagcaaac attgtaaacg tgccggaaca acaatctccg gagactgcgg    240
ccgtgtgcaa aaattaaaag ctgttgaata aactggaatc gagctcttac aacaaatcca    300
acattgacca gctggccgtt attgtaaagg atcctcaggt agtaagtatt cattgtaaat    360
ctgatattat ttgtattatt ataccctacct aatttgcagt gcagatcatt gagataatta    420
aaattataac catctcgcaa ataaataagt attttactgt tttcgtaaca gttttgtaat    480
aaaaaaacct ataaatccca ttacggcagt ataaattcgt tcatttttgga tattgtttca    540
gtgccggggt tttacgagat tgtgattaag gtccccagcg accttgacgg gcatctgccc    600
ggcatttctg acagctttgt gaactgggtg gccgagaagg agtgggagtt gccgccagat    660
tctgacttgg atctgaatct gattgagcag gcaccccgta ccggccgca gaagctgcag     720
cgcgactttc tgacgcgatg gcgccgtgtg agtaaggccc cggaggccct tttctttgtg    780
caatttgaga agggagagag ctacttccac ttacacgtgc tcgtggaaac caccggggtg    840
aaatcctttg ttttgggacg tttcctgagt cagattcgcg aaaaactgat tcagagaatt    900
taccgcggga tcgagccgac tttgccaaac tggttcgcgg tcacaaagac cagaaacggc    960
gccggaggcg ggaacaaggt ggtggacgag tgctacatcc ccaattactt gctccccaaa   1020
acccagcctg agctccagtg ggcgtggact aatttagaac agtatttaag cgcctgtttg   1080
aatctcacgg agcgtaaacg gttggtggcg cagcatctga cgcacgtgtc gcagacgcag   1140
gagcagaaca aagagaatca gaatcccaat tctgacgcgc cggtgatcag atcaaaaact   1200
tcagccaggt acatgagct ggtcgggtgg ctcgtgaca ggggattac ctcggagaag   1260
cagtggatcc aggaggacca ggcctcatac atctccttca atgcggcctc caactcgcgg   1320
tcccaaatca aggctgcctt ggacaatgcg ggaaagatta tgagcctgac taaaaccgcc   1380
cccgactacc tggtgggcca gcagcccgtg gaggacattt ccagcaatcg gatttataaa   1440
attttggaac taaacgggta cgatcccaa tatgcgggctt tctgggatgggcc   1500
acgaaaaagt tcggcaagag gaacaccatc tggctgtttg ggcctgcaac taccgggaag   1560
accaacatcg cggaggccat agcccacact gtgcccttct acgggtgcgt aaactggacc   1620
aatgagaact ttcccttcaa cgactgtgtc gacaagatgg tgatctggtg ggaggagggg   1680
aagatgaccg ccaaggtcgt ggagtcggcc aaagccattc tcggaggaaa caaggtgcgc   1740
gtggaccaga aatgcaagtc ctcggcccag atagacccga ctcccgtgat cgtcacctcc   1800
aacaccaaca tgtgcgccgt gattgacggg aactcaacga ccttcgaaca ccagcagccg   1860
ttgcaagacc ggatgttcaa atttgaactc acccgccgtc tggatcatga ctttgggaag   1920
gtcaccaagc aggaagtcaa agacttttc cggtgggcaa aggatcacgt ggttgaggtg   1980
gagcatgaat tctacgtcaa aaagggtgga gccaagaaaa gacccgcccc cagtgacgca   2040
gatataagtg agcccaaacg ggtgcgcgag tcagttgcgc agccatcgac gtcagacgcg   2100
gaagcttcga tcaactacgc agacaggtac caaaacaaat gttctcgtca cgtgggcatg   2160
aatctgatgc tgtttccctg cagacaatgc gagagaatga atcagaattc aaatatctgc   2220
ttcactcacg gacagaaaga ctgtttagag tgctttccg tgtcagaatc tcaacccgtt   2280
tctgtcgtca aaaaggcgta tcagaaactg tgctacattc atcatatcat gggaaaggtg   2340
ccagacgctt gcactgcctg cgatctggtc aatgtggatt tggatgactg catctttgaa   2400
caataa                                                              2406
SEQ ID NO: 7         moltype = DNA length = 2137
FEATURE              Location/Qualifiers
source               1..2137
                     mol_type = other DNA
                     note = artificial sequence
                     organism = unidentified
SEQUENCE: 7
gggagttcag tcgtcgaatg caaaacgtaa aaaatattaa taaggtaaaa actacagctg     60
gatcctcagg tagtaagtat tcattgtaaa tctgatatta tttgtattat tataccctacc   120
taatttgcag tgcagatcat tgagataatt aaaattataa ccatctcgca aataaataag    180
tattttactg ttttcgtaac agttttgtaa taaaaaaacc tataaatccc attacggcag    240
tataaattcg ttcattttgg atattgtttc agtgccgggg ttttacgaga ttgtgattaa    300
ggtccccagc gaccttgacg ggcatctgcc cggcatttct gacagctttg tgaactgggt    360
ggccgagaag gagtgggagt tgccgccaga ttctgacttg gatctgaatc tgattgagca    420
ggcacccctg accgtggccg agaagctgca gcgcgacttt ctgacggagt ggcgccgtgt    480
```

```
gagtaaggcc ccggaggccc ttttctttgt gcaatttgag aagggagaga gctacttcca    540
cttacacgtg ctcgtggaaa ccaccggggt gaaatcctta gttttgggac gtttcctgag    600
tcagattcgc gaaaaactga ttcagagaat ttaccgcggg atcgagccga ctttgccaaa    660
ctggttcgcg gtcacaaaga ccagaaacgg cgccggaggc gggaacaagg tggtggacga    720
gtgctacatc cccaattact tgctcccaa aacccagcct gagctccagt gggcgtggac     780
taatttagaa cagtatttaa gcgcctgttt gaatctcacg gagcgtaaac ggttggtggc    840
gcagcatctg acgcacgtgt cgcagacgca ggagcagaac aaagagaatc agaatcccaa    900
ttctgacgcg ccggtgatca gatcaaaaac ttcagccagg tacatggagc tggtcgggtg    960
gctcgtggac aagggattta cctcggagaa gcagtggatc caggaggacc aggcctcata    1020
catctccttc aatgcggcct ccaactcgcg gtcccaaatc aaggctgcct tggacaatgc    1080
gggaaagatt atgagcctga ctaaaaccgc ccccgactac ctggtgggcc agcagcccgt    1140
ggaggacatt tccagcaatc ggatttataa aattttggaa ctaaacgggt acgatcccca    1200
atatgcggct tccgtctttc tgggatgggc cacgaaaaag ttcggcaaga ggaacaccat    1260
ctggctgttt gggcctgcaa ctaccgggaa gaccaacatc gcggaggcca tagcccacac    1320
tgtgcccttc tacgggtgcg taaactggac caatgagaac tttcccttca acgactgtgt    1380
cgacaagatg gtgatctggt gggaggaggg gaagatgacc gccaaggtcg tggagtcggc    1440
caaagccatt ctcggaggaa gcaaggtgcg cgtggaccaa aaatgcaagt cctcggccca    1500
gatagacccg actcccgtga tcgtcacctc caacaccaac atgtgcgccg tgattgacgg    1560
gaactcaacg accttcgaac accagcagcc gttgcaagac cggatgttca aatttgaact    1620
cacccgccgt ctggatcatg actttgggaa ggtcaccaag caggaagtca aagacttttt    1680
ccggtgggca aaggatcacg tggttgaggt ggagcatgaa ttctacgtca aaaagggtgg    1740
agccaagaaa agacccgccc ccagtgacgc agatataagt gagcccaaac gggtgcgcga    1800
gtcagttgcg cagccatcga cgtcagacgc ggaagcttcg atcaactacg cagacaggta    1860
ccaaaacaaa tgttctcgtc acgtgggcat gaatctgatg ctgtttccct gcagacaatg    1920
cgagagaatg aatcagaatt caaatatctg cttcactcac ggacagaaag actgtttaga    1980
gtgctttccc gtgtcagaat ctcaacccgt ttctgtcgtc aaaaaggcgt atcagaaact    2040
gtgctacatt catcatatca tgggaaaggt gccagacgct tgcactgcct gcgatctggt    2100
caatgtggat ttggatgact gcatctttga acaataa                             2137

SEQ ID NO: 8            moltype = DNA   length = 2188
FEATURE                 Location/Qualifiers
source                  1..2188
                        mol_type = other DNA
                        note = artificial sequence
                        organism = unidentified
SEQUENCE: 8
gacctttaat tcaacccaac acaatatatt atagttaaat aagaattatt atcaaatcat    60
ttgtatatta attaaaatac tatactgtaa attacatttt atttacaatc ggatcctcag    120
gtagtaagta ttcattgtaa atctgatatt atttgtatta ttatacctac ctaatttgca    180
gtgcagatca ttgagataat taaaattata accatctcgc aaataaataa gtattttact    240
gttttcgtaa cagttttgta ataaaaaaac ctataaatcc cattacggca gtataaattc    300
gttcattttg gatattgttt cagtgccggg gttttacgag attgtgatta aggtccccag    360
cgaccttgac gggcatctgc ccggcatttc tgacagcttt gtgaactggg ttggccgagaa   420
ggagtgggag ttgccgccag attctgactt ggatctgaat ctgattgagc aggcacccct    480
gaccgtggcc gagaagctgc agcgcgactt tctgacggag tggcgccgtg tgagtaaggc    540
cccggaggcc ttttctttg tgcaatttga agggagag agctacttcc acttacacgt       600
gctcgtggaa accaccgggg tgaaatcctt agttttggac cgtttcctga gtcagattcg    660
cgaaaaactg attcagagaa tttaccgcgg gatcgagccg actttgccaa actggttcgc    720
ggtcacaaag accagaaacg cgccggagg cgggaacaag gtggtggacg agtgctacat     780
ccccaattac ttgctcccca aacccagcct gagctccag tgggcgtgga ctaatttaga    840
acagtatttta agcgcctgtt tgaatctcac ggagcgtaaa cggttggtgg cgcagcatct   900
gacgcacgtg tcgcagacgc aggagcagaa caaagagaat cagaatccca attctgacgc    960
gccggtgatc agatcaaaaa cttcagccag gtacatggag ctggtcgggt ggctcgtgga    1020
caaggggatt acctcggaga agcagtggat ccaggaggac caggcctcat acatctcctt    1080
caatgcggc tccaactcgc ggtcccaaat caaggctgcc ttggacaatg cgggaaagat    1140
tatgagcctg actaaaaccg ccccgacta cctggtgggc cagcagcccg tggaggacat    1200
ttccagcaat cggattttata aaattttgga actaaacggg tacgatcccc aatatgcggc   1260
ttccgtcttt ctgggatggg ccacgaaaaa gttcggcaag aggaacacca tctggctgtt    1320
tgggcctgca actaccggga agaccaacat cgcggaggcc atagcccaca ctgtgccctt    1380
ctacgggtgc gtaaactgga ccaatgagaa ctttcccttc aacgactgtg tcgacaagat    1440
ggtgatctgg tgggaggagg ggaagatgac cgccaaggtc gtggagtcgg ccaaagccat    1500
tctcggagga agcaaggtgc gcgtggacca aaaatgcaag tcctcggccc agatagaccc    1560
gactcccgtg atcgtcacct ccaacaccaa catgtgcgcc gtgattgacg ggaactcaac    1620
gaccttcgaa caccagcagc cgttgcaaga ccggatgttc aaatttgaac tcacccgccg    1680
tctggatcat gactttggga aggtcaccaa gcaggaagtc aaagactttt ccggtgggc    1740
aaaggatcac gtgttgagg tggagcatga attctacgtc aaaaagggtg gagccaagaa    1800
aagacccgcc cccagtgacg cagatataag tgagcccaaa cgggtgcgcg agtcagttgc    1860
gcagccatcg acgtcagacg cggaagcttc gatcaactac gcagacaggt accaaaacaa    1920
atgttctcgt cacgtgggca tgaatctgat gctgtttccc tgcagacaat gcgagagaat    1980
gaatcagaat tcaaatatct gcttcactca cggacagaaa gactgtttag agtgctttcc    2040
cgtgtcagaa tctcaacccg tttctgtcgt caaaaaggcg tatcagaaac tgtgctacat    2100
tcatcatatc atgggaaagg tgccagacgc ttgcactgcc tgcgatctgg tcaatgtgga    2160
tttggatgac tgcatctttg aacaataa                                       2188

SEQ ID NO: 9            moltype = DNA   length = 2379
FEATURE                 Location/Qualifiers
source                  1..2379
                        mol_type = other DNA
                        note = artificial sequence
```

```
                        organism = unidentified
SEQUENCE: 9
atcattgaga taattaaaat tataaccatc tcgcaaataa ataagtattt tactgttttc    60
gtaacagttt tgtaataaaa aaacctataa atattccgga ttattcatac cgtcccacca   120
tcgggcgcgg atcccagcag gtaagtatcg ataactttgt tttctttcac atttacaact   180
ccgacataca aatatgaata aacgataacg ccgttggtgg cgtgaggcat gtaaaaggtt   240
acatcattat cttgttcgcc atccggttgg tataaataga cgttcatgtt ggtttttgtt   300
tcagttgcaa gttggctgcg gcgcgcgcag cacctttgcg taagccgcca gtaagtattc   360
attgtaaatc tgatattatt tgtattatta tacctaccta atttgcagtg cagggtaatt   420
ttattactgt ttggtccata aacacttgtt taccatttcc ttttttacaa gttttaatat   480
tttctgcata tataaaacat tatttatttt gcagtgccgg ggttttacga gattgtgatt   540
aaggtcccca gcgaccttga cgggcatctg cccggcattt ctgacagctt tgtgaactgg   600
gtggccgaga aggagtggga gttgccgcca gattctgact tggatctgaa tctgattgag   660
caggcacccc tgaccgtggc cgagaagctg cagcgcgcct ttctgacgga gtggcgccag   720
gtgagtaagg ccccggaggc ccttttcttt gtgcaatttg agaagggaga gagctacttc   780
cacttacacg tgctcgtgga aaccaccggg gtgaaatcct tagttttggg acgtttcctg   840
agtcagattc gcgaaaaact gattcagaga atttaccgcg ggatcgagcc gactttgcca   900
aactggttcg cggtcacaaa gaccagaaac ggcgccggaa ggtggtggac   960
gagtgctaca tccccaatta cttgctcccc aaaacccagc ctgagctcca gtgggcgtgg  1020
actaatttag aacagtattt aagcgcctgt ttgaatctca cggagcgtaa acggttggtg  1080
gcgcagcatc tgacgcacgt gtcgcagacg caggagcaga acaaagagaa tcagaatccc  1140
aattctgacg cgccggtgat cagatcaaaa acttcagcca gctacatgga gctggtcggg  1200
tggctcgtgg acaaggggat tacctcggag aagcagtgga tccaggagga ccaggcctca  1260
tacatctcct tcaatgcggc ctccaactcg cggtcccaaa tcaaggctgc cttggacaat  1320
gcgggaaaga ttatgagcct gactaaaacc gcccccgact acctggtggg ccagcagccc  1380
gtggaggaca tttccagcaa tcggatttat aaaattttgg aactaaacgg gtacgatccc  1440
caatatgcgg cttccgtctt tctgggatgg gccacgaaaa agttcggcaa gaggaacacc  1500
atctggctgt ttgggcctgc aactaccggg aagaccaaca tcgcggaggc catagcccac  1560
actgtgccct tctacgggtg cgtaaactgg accaatgaga ctttcccctt caacgactgt  1620
gtcgacaaga tggtgatctg gtgggaggag gggaagatga ccgccaaggt gctggagtcg  1680
gccaaagcca ttctcggagg aagcaaggtg cgcgtggacc agaaatgcaa gtcctcggcc  1740
cagatagacc cgactcccgt gatcgtcacc tccaacacca acatgtgcgc cgtgattgac  1800
gggaactcaa cgaccttcga acaccagcag ccgttgcaag accggatgtt caaatttgaa  1860
ctcacccgcc gtctggatca tgactttggg aaggtcacca agcaggaagt caaagacttt  1920
ttccggtggg caaggatca cgtggttgag gtggagcatg aattctacgt caaaaagggt  1980
ggagccaaga aaagacccgc ccccagtgac gcagatataa gtgagcccaa acgggtgcgc  2040
gagtcagttg cgcagccatc gacgtcagac gcggaagctt cgatcaacta cgcagacagg  2100
taccaaaaca aatgttctcg tcacgtgggc atgaatctga tgctgttttcc ctgcagacaa  2160
tgcgagagaa tgaatcagaa ttcaaaatatc tgcttcactc acggacagaa agactgttta  2220
gagtgctttc ccgtgtcaga atctcaaccc gtttctgtcg tcaaaaaggc gtatcagaaa  2280
ctgtgctaca ttcatcatat catgggaaag gtgccagacg cttgcactgc ctgcgatctg  2340
gtcaatgtgg atttggatga ctgcatcttt gaacaataa                         2379

SEQ ID NO: 10          moltype = DNA   length = 2560
FEATURE                Location/Qualifiers
source                 1..2560
                       mol_type = other DNA
                       note = artificial sequence
                       organism = unidentified
SEQUENCE: 10
atcattgaga taattaaaat tataaccatc tcgcaaataa ataagtattt tactgttttc    60
gtaacagttt tgtaataaaa aaacctataa atattccgga ttattcatac cgtcccacca   120
tcgggcgcgg atcccagcag gtaagtatcg ataactttgt tttctttcac atttacaact   180
ccgacataca aatcacatgt tggacatcgt gtcgtttgag cgtataaaag aatatataag   240
agctaattta ggccatttca cagtaatcac cgacaaatgt cgaagcgta aggtgtgtct   300
tcatcacaaa cgaattgcca ggttgttggg cattaaaaaa atatatcatc aagaataacaa   360
acggggttgtt tcaaaggttt acaagaagca aacattgtaa acgtgccgga gcaacaatct   420
ccggagactg cggccgtgtg caaaaattaa aagctgttga ataaactgga atcgagctct   480
tacaacaaat ccaacattga ccagctggcc gttattgtaa aaaagccgcc agtaagtatt   540
cattgtaaat ctgatattat ttgtattatt ataccatacct aatttgcagt gcagggtaat   600
tttattactg tttggtccat aaacacttgt ttaccatttc ctttttttaca agttttaata   660
ttttctgcat atataaaaca ttatttattt tgcagtgccg ggttttacga gattgtgatt   720
taaggtcccc agcgaccttg acgggcatct gcccggcatt tctgacagct tgtgaactg   780
ggtggccgag aaggagtggg agttgccgcc agattctgac ttggatctga atctgattga   840
gcaggcaccc ctgaccgtgg ccgagaagct gcagcgcgca tttctgacgg agtggcgccg   900
tgtgagtaag gccccggagg ccttttcttt gtgcaatttt gagaagggag agagctactt   960
ccacttacac gtgctcgtgg aaaccaccgg ggtgaaatcc ttagttttgg gacgtttcct  1020
gagtcagatt cgcgaaaaac tgattcagag aatttaccgc gggatcgagc cgactttgcc  1080
aaactggttc gcggtcacaa agaccagaaa cggcgccgga aggtggtgga  1140
cgagtgctac atccccaatt acttgctccc caaacccag cctgagctcc agtgggcgtg  1200
gactaattta gaacagtatt taagcgcctg tttgaatctc acggagcgta aacggttggt  1260
ggcgcagcat ctgacgcacg tgtcgcagac gcaggagcag aacaaagaga atcagaatcc  1320
caattctgac gcgccggtga tcagatcaaa aacttcagcc aggtacatgg agctggtcgg  1380
gtggctcgtg gacaagggga ttacctcgga agcagtgga tccaggagga ccaggccca  1440
atacatctcc ttcaatgcgg cctccaactc gcgtcccaa atcaaggctg ccttggacaa  1500
tgcgggaaag attatgagcc tgactaaaac cgcccccgac tacctggtgg gccagcagcc  1560
cgtggaggac atttccagca atcggattta taaaattttg gaactaaacg ggtacgatcc  1620
ccaatatgcg gcttccgtct ttctgggatg gccacgaaa agttcggca agaggaacac  1680
catctggctg tttgggcctg caactaccgg gaagaccaac atcgcggagg ccatagccca  1740
```

```
cactgtgccc ttctacgggt gcgtaaactg gaccaatgag aactttccct tcaacgactg   1800
tgtcgacaag atggtgatct ggtggggagga ggggaagatg accgccaagg tcgtggagtc   1860
ggccaaagcc attctcggag gaagcaaggt gcgcgtggac cagaaatgca agtcctcggc   1920
ccagatagac ccgactccg tgatcgtcac ctccaacacc aacatgtgcg ccgtgattga   1980
cgggaactca acgaccttcg aacaccagca gccgttgcaa gaccggatgt tcaaatttga   2040
actcacccgc cgtctggatc atgactttg gaaggtcacc aagcaggaag tcaaagactt   2100
tttccggtgg gcaaaggatc acgtggttga ggtggagcat gaattctacg tcaaaaaggg   2160
tggagccaag aaaagacccg ccccagtga cgcagatata agtgagccca aacgggtgcg   2220
cgagtcagtt gcgcagccat cgacgtcaga cgcggaagct tcgatcaact acgcagacag   2280
gtaccaaaac aaatgttctc gtcacgtggg catgaatctg atgctgtttc cctgcagaca   2340
atgcgagaga atgaatcaga attcaaatat ctgcttcact cacggacaga aagactgttt   2400
agagtgcttt cccgtgtcag aatctcaacc cgtttctgtc gtcaaaaagg cgtatcagaa   2460
actgtgctac attcatcata tcatgggaaa ggtgccagac gcttgcactg cctgcgatct   2520
ggtcaatgtg gatttggatg actgcatctt tgaacaataa                         2560

SEQ ID NO: 11           moltype = DNA   length = 2294
FEATURE                 Location/Qualifiers
source                  1..2294
                        mol_type = other DNA
                        note = artificial sequence
                        organism = unidentified
SEQUENCE: 11
atcattgaga taattaaaat tataaccatc tcgcaaataa ataagtattt tactgttttc    60
gtaacagttt tgtaataaaa aaacctataa atattccgga ttattcatac cgtcccacca   120
tcgggcgcgg atcccagcag gtaagtatcg ataactttgt tttctttcac atttacaact   180
ccgacataca aatatgggga gttcagtcgt cgaatgcaaa acgtaaaaaa tattaataag   240
gtaaaaacta cagcttaagc cgccagtaag tattcattgt aaatctgata ttatttgtat   300
tattatacct acctaatttg cagtgcaggg taatttatt actgtttggt ccataaacac   360
ttgtttacca tttcctttt tacaagtttt aatattttct gcatatataa aacattattt   420
attttgcagt gccggggttt tacgagattg tgattaaggt ccccagcgcc cttgacgggg   480
atctgcccgg catttctgac agctttgtga actgggtggc cgagaaggag tgggagttgc   540
cgccagattc tgacttggat ctgaatctga ttgagcaggc accctgacc gtggccgaga   600
agctgcagcg cgactttctg acggagtggc gccgtgtgag taaggccccg gaggcccttt   660
tctttgtgca atttgagaag ggagagagct acttccactt acacgtgctc gtggaaacca   720
ccggggtgaa atccttagtt ttgggacgtt tcctgagtca gattcgcgaa aaactgattc   780
agagaattta ccgcgggatc gagccgactt tgccaaactg gttcgcggtc acaaagacca   840
gaaacggcgc cggaggcggg aacaaggtgg tggacgagtg ctacatcccc aattacttgc   900
tccccaaaac ccagcctgag ctccagtggg cgtggactaa tttagaacag tatttaagcg   960
cctgttttgaa tctcacggag cgtaaacggt tggtggcgca gcatctgacg cacgtgtcgc  1020
agacgcagga gcagaacaaa gagaatcaga atcccaattc tgacgcgccg gtgatcagat  1080
caaaaacttc agccaggtac atggagctgg tcggtggct cgtggacaag gggattacct  1140
cggagaagca gtggatccag gaggaccagg cctcatacat ctccttcaat gcggcctcca  1200
actcgcggtc ccaaatcaag gctgccttgg acaatgcggg aaagattatg agcctgacta  1260
aaaccgcccc cgactacctg gtgggccagc agcccgggga ggacatttcc agcaatcgga  1320
tttataaaat tttggaacta aacgggtacg atccccaata tgcggcttcc gtcttttctgg 1380
gatgggccac gaaaaagttc ggcaagagga acaccatctg gctgtttggg cctgcaacta  1440
ccgggaagac caacatgcg gaggccatag cccacactgt gccccttctac gggtgcgtaa  1500
actggaccaa tgagaacttt cccttcaacg actgtgtcga caagatggtg atctggtggg  1560
aggaggggaa gatgaccgcc aaggtcgtgg agtcggccaa agccattctc ggaggaagca  1620
aggtgcgcgt ggaccagaaa tgcaagtcct cggcccagat agaccccgact cccgtgatcg  1680
tcacctccaa caccaacatg tgcgccgtga ttgacgggaa ctcaacgacc ttcgaacacc  1740
agcagccgtt gcaagaccgg atgttcaaat ttgaactcac ccgccgtctg gatcatgact  1800
ttgggaaggt caccaagcag gaagtcaaag acttttttccg gtgggcaaag gatcacgtgg  1860
ttgaggtgga gcatgaattc tacgtcaaaa agggtggagc caagaaaaga cccgccccca  1920
gtgacgcaga tataagtgag cccaaacggg tgcgcgagtc agttgcgcag ccatcgacgt  1980
cagacgcgga agcttcgatc aactacgcag acaggtacca aaacaaatgt tctcgtcacg  2040
tgggcatgaa tctgatgctg tttccctgca gacaatgcga gagaatgaat cagaattcaa  2100
atatctgctt cactcacgga cagaaagact gtttagagtg cttttccgtg tcagaatctc  2160
aacccgtttc tgtcgtcaaa aaggcgtatc agaaactgtg ctacattcat catatcatgg  2220
gaaaggtgcc agacgcttgc actgcctgcg atctggtcaa tgtggatttg gatgactgca  2280
tctttgaaca ataa                                                    2294

SEQ ID NO: 12           moltype = DNA   length = 2345
FEATURE                 Location/Qualifiers
source                  1..2345
                        mol_type = other DNA
                        note = artificial sequence
                        organism = unidentified
SEQUENCE: 12
atcattgaga taattaaaat tataaccatc tcgcaaataa ataagtattt tactgttttc    60
gtaacagttt tgtaataaaa aaacctataa atattccgga ttattcatac cgtcccacca   120
tcgggcgcgg atcccagcag gtaagtatcg ataactttgt tttctttcac atttacaact   180
ccgacataca aatatggacc tttaattcaa cccaacacaa tatattatag ttaaataaga   240
attattatca atcattttgt atattaatta aaatactata ctgtaaatta cattttattt   300
acaatctaag ccgccagtaa gtattcattg taaatctgat attatttgta ttattatacc   360
tacctaatttt gcagtgcagg gtaatttttat tactgtttgg tccataaaca cttgtttacc   420
atttcctttt ttacaagttt taatattttc tgcatatata aaacattatt tattttgcag   480
tgccggggtt ttacgagatt gtgattaagg tccccagcgc ccttgacggg catctgcccg   540
gcatttctga cagctttgtg aactgggtgg ccgagaagga gtgggagttg ccgccagatt   600
```

```
ctgacttgga tctgaatctg attgagcagg caccccctgac cgtgccgag aagctgcagc   660
gcgactttct gacggagtgg cgccgtgtga gtaaggcccc ggaggccctt ttctttgtgc    720
aatttgagaa gggagagagc tacttccact tacacgtgct cgtggaaacc accggggtga   780
aatccttagt tttgggacgt ttcctgagtc agattcgcga aaaactgatt cagagaattt    840
accgcgggat cgagccgact ttgccaaact ggttcgcgaa cacaaagacc agaaacggcg    900
ccggaggcgg gaacaaggtg gtggacgagt gctacatccc caattacttg ctcccccaaaa   960
cccagcctga gctccagtgg gcgtggacta atttagaaca gtatttaagc gcctgtttga   1020
atctcacgga gcgtaaacgg ttggtggcgc agcatctgac gcacgtgtcg cagacgcagg   1080
agcagaacaa agagaatcag aatcccaatt ctgacgcgcc ggtgatcaga tcaaaaactt   1140
cagccaggta catggagctg gtcgggtggc tcgtggacaa ggggattacc tcggagaagc   1200
agtggatcca ggaggaccag gcctcataca tctccttcaa tgcggcctcc aactcgcggt   1260
cccaaatcaa ggctgccttg acaatgcgg gaaagattat gagcctgact aaaaccgccc   1320
ccgactacct ggtgggccag cagcccgtgg aggacatttc cagcaatcgg atttataaaa   1380
ttttggaact aaacgggtac gatccccaat atgcggcttc cgtcttttctg ggatgggca   1440
cgaaaaagtt cggcaagagg aacaccatct ggctgtttgg gcctgcaact accgggaaga   1500
ccaacatcgc ggaggccata gcccacactg tgcccttcta cgggtgcgta aactggacca   1560
atgagaactt tcccttcaac gactgtgtcg acaagatggt gatctggtgg gaggagggga   1620
agatgaccgc caaggtcgtg gagtcggcca aagccattct cggaggaagc aaggtgcgg   1680
tggaccagaa atgcaagtcc tcggcccaga tagacccgac tcccgtgatc gtcacctcca   1740
acaccaacat gtgcgccgtg attgacggga actcaacgac cttcgaacac cagcagccgt   1800
tgcaagaccg gatgttcaaa tttgaactca cccgccgtct ggatcatgac tttgggaagg   1860
tcaccaagca ggaagtcaaa gacttttttcc ggtgggcaaa ggatcacgtg gttgaggtgg   1920
agcatgaatt ctacgtcaaa aagggtggag ccaagaaaag acccgccccc agtgacgcag   1980
atataagtga gcccaaacgg gtgcgcgagt cagttgcgca gccatcgacg tcagacgcgg   2040
aagcttcgat caactacgca gacaggtacc aaaaacaaatg ttctcgtcac gtgggcatga   2100
atctgatgct gtttccctgc agacaatgcg agagaatgaa tcagaattca aatatctgct   2160
tcactcacgg acagaaagac tgtttagagt gctttcccgt gtcagaatct caacccgttt   2220
ctgtcgtcaa aaaggcgtat cagaaactgt gctacattca tcatatcatg ggaaaggtgc   2280
cagacgcttg cactgcctgc gatctggtca atgtggatttt ggatgactgc atctttgaac   2340
aataa                                                              2345

SEQ ID NO: 13          moltype = DNA   length = 2079
FEATURE                Location/Qualifiers
source                 1..2079
                       mol_type = other DNA
                       note = artificial sequence
                       organism = unidentified
SEQUENCE: 13
atcattgaga taattaaaat tataaccatc tcgcaaataa ataagtattt tactgttttc    60
gtaacagttt tgtaataaaa aaacctataa attggatcct caggtagtaa gtattcattg   120
taaatctgat attatttgta ttattatacc tacctaattt gcagtgcagc ccattacggc   180
agtataaatt cgttcatttt ggatattgtt tcagtgccgg ggttttacga gattgtgatt   240
aaggtcccca gcgaccttga cgggcatctg cccggcattc ctgacagctt tgtgaactga   300
gtggccgaga aggagtggga gttgccgcca gattctgact tggatctgaa tctgattgag   360
caggcacccc tgaccgtggc cgagaagctg cagcgcgact ttctgacgga gtggcgccgt   420
gtgagtaagg ccccggaggc ccttttcttt gtgcaatttg agaagggaga gagctacttc   480
cacttacacg tgctcgtgga aaccaccggg tgaaatcctt agttttggg acgtttcctg   540
agtcagattc gcgaaaaact gattcagaga atttaccgcg ggatcgagcc gactttgcca   600
aactggttcg cggtcacaaa gaccagaaac ggcgccggag gcgggaacaa ggtggtggac   660
gagtgctaca tccccaatta cttgctcccc aaaacccagc ctgagctcca gtgggcgtgg   720
actaatttag aacagtattt aagcgcctgt ttgaatctca cggagcgtaa acggttgctg   780
gcgcagcatc tgacgcacgt gtcgcagacg caggagcaga acaaagaaa tcagaatccc   840
aattctgacg cgccggtgat cagatcaaaa acttcagcca ggtacatgga gctggtcggg   900
tggctcgtgg acaagggga tacctcggag aagcagtgga tccaggagga ccaggcctca   960
tacatctcct tcaatgcggc ctccaactcg cggtcccaaa tcaaggctgc cttggacaat   1020
gcgggaaaga ttatgagcct gactaaaacc gccccccgact acctggtggg ccagcagccc   1080
gtggaggaca tttccagcaa tcggatttat aaaattttgg aactaaacgg gtacgatccc   1140
caatatgcgg cttccgtctt tctgggatgg gccacgaaaa agttcggcaa gaggaacacc   1200
atctggctgt ttgggcctgc aactaccggg aagaccaaca tcgcggaggc catagcccac   1260
actgtgccct tctacgggtg cgtaaactgg accaatgaga actttccctt caacgactgt   1320
gtcgacaaga tggtgatctg tgggaggag gggaagatga ccgccaaggt cgtggagtcg   1380
gccaaagcca ttctcggagg aagcaaggtg cgcgtggacc agaaatgcaa gtcctcggcc   1440
cagatagacc cgactcccgt gatcgtcacc tccaacacca catgtgcgc cgtgattgac   1500
gggaactcaa cgaccttcga acaccagcag ccgttgcaag gacgatgtt caaatactttaa   1560
ctcacccgcc gtctggatca tgactttggg aaggtcacca agcaggaagt caaagacttt   1620
ttccggtggg caaaggatca cgtggttgag gtggagcatg aattctacgt caaaaagggt   1680
ggagccaaga aaagacccgc ccccagtgac gcagatataa gtgagcccaa acgggtgcgc   1740
gagtcagttg cgcagccatc gacgtcagac gcggaagctt cgatcaacta cgcagacagg   1800
taccaaaaaca aatgttctcg tcacgtgggc atgaatctga tgctgtttcc ctgcagacaa   1860
tgcgagagaa tgaatcagaa ttcaaatatc tgcttcactc acggacagaa agactgttta   1920
gagtgctttc ccgtgtcaga atctcaaccc gtttctgtcg tcaaaaaggc gtatcagaaa   1980
ctgtgctaca ttcatcatat catgggaaag gtgccagacg cttgcactgc ctgcgatctg   2040
gtcaatgtgg atttggatga ctgcatcttt gaacaataa                          2079

SEQ ID NO: 14          moltype = DNA   length = 2130
FEATURE                Location/Qualifiers
source                 1..2130
                       mol_type = other DNA
                       note = artificial sequence
```

```
                        organism = unidentified
SEQUENCE: 14
aataaacgat aacgccgttg gtggcgtgag gcatgtaaaa ggttacatca ttatcttgtt    60
cgccatccgg ttggtataaa tagacgttca tgttggtttt tgtttcagtt gcaagttggc   120
tgcggcgcgc gcagcacctt tgcgggatcc tcaggtagta agtattcatt gtaaatctga   180
tattatttgt attattatac ctacctaatt tgcagtgcag cccattacgg cagtatgaat   240
tcgttcattt tggatattgt ttcagtgccg gggttttacg agattgtgat taaggtcccc   300
agcgaccttg acgggcatct gcccggcatt tctgacagct tgtgaactg ggtggccgag    360
aaggagtggg agttgccgcc agattctgac ttggatctga atctgattga gcaggcaccc   420
ctgaccgtgg ccgagaagct gcagcgcgac tttctgacgg agtgcgccg tgtgagtaag    480
gccccggagg ccctttttctt tgtgcaattt gagaagggag agagctactt ccacttacac   540
gtgctcgtgg aaaccaccgg ggtgaaatcc ttagttttgg gacgtttcct gagtcagatt    600
cgcgaaaaac tgattcagag aatttaccgc gggatcgagc cgactttgcc aaactggttc   660
gcggtcacaa agaccagaaa cggcgccgga ggcgggaaca aggtggtgga cgagtgctac   720
atccccaatt acttgctccc caaacccag cctgagctcc agtgggcgtg gactaattta    780
gaacagtatt taagcgcctg tttgaatctc acggagcgta aacggttggt ggcgcagcat   840
ctgacgcacg tgtcgcagac gcaggagcag aacaaagaga atcagaatcc caattctgac   900
gcgccggtga tcagatcaaa aacttcagcc aggtacatgg agctggtcgg gtggctcgtg   960
gacaagggga ttacctcgga gaagcagtgg atccaggagg accaggcctc atacatctcc  1020
ttcaatgcgg cctccaactc gcggtcccaa atcaaggctg ccttggacaa tgcgggaaag  1080
attatgagcc tgactaaaac cgcccccgac tacctggtgg ccagcagcc cgtggaggac   1140
atttccagca atcggattta taaaattttg gaactaagtg agtacgatcc tccaatatgc   1200
gcttccgtct ttctgggatg ggccacgaaa aagttcggca agaggaacac catctgctg   1260
tttgggcctg caactaccgg gaagaccaac atcgcggagg ccatagccca cactgtgccc  1320
ttctacgggt gcgtaaactg gaccaatgag aactttccct tcaacgactg tgtcgacaag   1380
atggtgatct ggtgggagga ggggaagatg accgccaaga tcgtgagtc ggccaaagcc   1440
attctcggag gaagcaaggt gcgcgtggac cagaaatgca agtcctcggc ccagatagac   1500
ccgactcccg tgatcgtcac ctccaacacc aacatgtgcg ccgtgattga cgggaactca   1560
acgaccttcg aacaccagca gccgttgcaa gaccggatgt tcaaatttga actcaccgc    1620
cgtctggatc atgactttgg gaaggtcacc aagcaggaag tcaaagactt tttccggtgg   1680
gcaaaggatc acgtggttga ggtggagcat gaattctacg tcaaaaaggg tggagccaag   1740
aaaagacccg ccccagtga cgcagatata agtgagccca acgggtgcg cgagtcagtt    1800
gcgcagccat cgacgtcaga cgcggaagct tcgatcaact acgcagacag gtaccaaaac  1860
aaatgttctc gtcacgtggg catgaatctg atgctgtttc cctgcagaca atgcgagaga   1920
atgaatcaga attcaaatat ctgcttcact cacggacgaa aagactgttt agagtgcttt   1980
cccgtgtcag aatctcaacc cgtttctgtc gtcaaaaagg cgtatcagaa actgtgctac   2040
attcatcata tcatgggaaa ggtgccagac gcttgcactg cctgcgatct ggtcaatgtg   2100
gatttggatg actgcatctt tgaacaataa                                    2130

SEQ ID NO: 15          moltype = DNA   length = 2314
FEATURE                Location/Qualifiers
source                 1..2314
                       mol_type = other DNA
                       note = artificial sequence
                       organism = unidentified
SEQUENCE: 15
cacatgttgg acatcgtgtc gtttgagcgt ataaaagaat atataagagc taatttaggc    60
catttcacag taatcaccga caaatgttcg aagcgtaagg tgtgtcttca tcacaaacga   120
attgccaggt tgtttgggcat taaaaaaata tatcatcaag aatacaaacg ggttgtttca   180
aaggtttaca agaagcaaac attgtaaacg tgccggagca acaatctccg gagactgcgg   240
ccgtgtgcaa aaattaaag ctgttgaata aactggaatc gagctcttac aacaaatcca    300
acattgacca gctggccgtt attgtaaagg atcctcaggt agtaagtatt cattgtaaat   360
ctgatattat ttgtattatt ataccctacct aatttgcagt gcagcccatt acggcagtat   420
aaattcgttc attttggata ttgtttcagt gccggggttt tacgagattg tgattaaggt   480
ccccagcgac cttgacgggc atctgcccgg catttctgac agctttgtga actgggtggc   540
cgagaaggag tggggagttgc cgccagattc tgacttggat ctgaatctga ttgagcaggc   600
accctgacc gtgccgaga gctgcagcg cgactttctg acggagtggc gccgtgtgag   660
taaggccccg gaggcccttt tctttgtgca atttgagaag ggagagagct acttccactt   720
acacgtgctc gtggaaacca ccggggtgaa atccttagtt ttgggacgtt tcctgagtca   780
gattcgcgaa aaactgattc agagaatttta ccgcgggatc gagccgactt tgccaaactg   840
gttcgcggtc acaaagacca gaaacggcgc cggaggcggg aacaaggtgg tggacgagtg   900
ctacatcccc aattacttgc tccccaaaac ccagcctgag ctccagtggg cgtggactaa   960
tttagaacag tatttaagcg cctgtttgaa tctcacggag cgtaaacggt tggtggcgca  1020
gcatctgacg cacgtgtcgc agacgcagga gcagaacaaa gagaatcaga atcccaattc  1080
tgacgcgccg gtgatcagat caaaaacttc agccaggtac atggagctgg tcgggtggct  1140
cgtggacaag gggattacct cggagaagca gtggatccag gaggaccagg cctcatacat  1200
ctccttcaat gcgcctcca actcgcggtc ccaaatcaag gctgcttgg acaatgcggg   1260
aaagattatg agcctgacta aaaccgcccc cgactacctg gtggccagc agccgtgga    1320
ggacatttcc agcaatcgga tttataaaat tttggaacta agtgagtacg atccccaata  1380
tgcggcttcc gtctttctgg gatgggccac gaaaaagttc ggcaagagga acaccatctg  1440
gctgtttggg cctgcaacta ccgggaagac caacatcgcg gaggcatag cccacactgt   1500
gcccttctac gggtgcgtaa actggaccaa tgagaacttt cccttcaacg actgtgtcga  1560
caagatggtg atctggtggg aggaggggaa gatgaccgcc aaggtcgtgg agtcggccaa  1620
agccattctc ggaggaaagca aggtgcgcgt ggaccagata gcaagtcct cggcccagat    1680
agacccgact cccgtgatcg tcacctccaa caccaacatg tgccgcgtga ttgacgggaa  1740
ctcaacgacc ttcgaacacc agcagccgtt gcaagaccgg atgttcaaat ttgaactcac  1800
ccgccgtctg gatcatgact ttgggaaggt caccaagcag gaagtcaaag acttttccg    1860
gtgggcaaag gatcacgtgg ttgaggtgga gcatgaattc tacgtcaaaa agggtggagc  1920
caagaaaaga cccgccccca gtgacgcaga tataagtgag cccaaacggg tgcgcgagtc  1980
```

```
agttgcgcag ccatcgacgt cagacgcgga agcttcgatc aactacgcag acaggtacca    2040
aaacaaatgt tctcgtcacg tgggcatgaa tctgatgctg tttccctgca gacaatgcga    2100
gagaatgaat cagaattcaa atatctgctt cactcacgga cagaaagact gtttagagtg    2160
cttttcccgt tcagaatctc aacccgtttc tgtcgtcaaa aaggcgtatc agaaactgtg    2220
ctacattcat catatcatgg gaaaggtgcc agacgcttgc actgcctgcg atctggtcaa    2280
tgtggatttg gatgactgca tctttgaaca ataa                                2314

SEQ ID NO: 16           moltype = DNA   length = 2045
FEATURE                 Location/Qualifiers
source                  1..2045
                        mol_type = other DNA
                        note = artificial sequence
                        organism = unidentified
SEQUENCE: 16
gggagttcag tcgtcgaatg caaaacgtaa aaaatattaa taaggtaaaa actacagctg     60
gatcctcagg tagtaagtat tcattgtaaa tctgatatta tttgtattat tatacctacc    120
taatttgcag tgcagcccat tacggcagta taaattcgtt cattttggat attgtttcag    180
tgccgggggtt ttacgagatt gtgattaagg tccccagcgg ccttgacggg catctgcccg   240
gcatttctga cagctttgtg aactgggtgg ccgagaagga gtgggagttg ccgccagatt    300
ctgacttgga tctgaatctg attgagcagg caccctgac cgtggccgag aagctgcagc    360
gcgacttcct gacggagtgg cgccgtgtga gtaaggcccc ggaggccctt ttctttgtgc    420
aatttgagaa gggagagagc tacttccact tacacgtcgt tggaaacc accggggtga    480
aatccttagt tttgggacgt ttcctgagtc agattcgcga aaaactgatt cagagaatt    540
accgcgggat cgagccgact ttgccaaact ggttcgcggt cacaaagacc agaaacggcg    600
ccggaggcgg gaacaaggtg gtggacgagt gctacatccc caattacttg ctccccaaaa    660
cccagcctga gctccagtgg gcgtggacta atttagaagt gtatttaagc gcctgtttga    720
atctcacgga gcgtaaacgg ttggtggcgc agcatctgac gcacgtgtcg cagacgcagg    780
agcagaacaa agagaatcag aatcccaatt ctgacgcgcc ggtgatcaga tcaaaaactt    840
cagccaggta catggagctg tcggtggc tcgtggacaa ggggattacc tcggagaagc     900
agtggatcca ggaggaccag gcctcataca tctccttcaa tgccgcctcc aactcgcgga    960
cccaaatcaa ggctgccttg acaatgcgg gaaagattat gagcctgact aaaaccgccc    1020
ccgactacct ggtgggccag cagcccgtgg aggacatttc cagcaatcgg atttataaaa    1080
ttttggaact aaacgggtac gatccccaat atgcggcttc cgtctttctg ggatgggcca    1140
cgaaaaagtt cggcaagagg aacaccatct ggctgtttgg gcctgcaact accgggaaga    1200
ccaacatcgc ggaggccata gcccacactg tgccctcta cgggtgcgta aactggacca    1260
atgagaactt tcccttcaac gactgtcgcg acaagatggt gatctggtgg gaggaggga    1320
agatgaccgc caaggtcgtg gagtcggcca agccattct cggaggaagc aaggtgcgcg    1380
tggaccagaa atgcaagtcc tcggcccaga tagacccgac tcccgtgatc gtcacctcca    1440
acaccaacat gtgcgccgtg attgacggga actcaacgac cttcgaacac cagcagccgt    1500
tgcaagaccg gatgttcaaa tttgaactca cccgccgtct ggatcatgac tttgggaagg    1560
tcaccaagca ggaagtcaaa gacttttttcc ggtgggcaaa ggatcacgtg gttgaggtgg    1620
agcatgaatt ctacgtcaaa aagggtgtgag ccaagaaaag acccgccccc agtgacgcag    1680
atataagtga gcccaaacgg gtgcgcgagt cagttgcgca cgcatcgacg tcagacgcgg    1740
aagcttcgat caactacgca gacaggtacc aaaacaaatg ttctcgtcac gtgggcatga    1800
atctgatgct gtttccctgc agacaatgcg agagaatgaa tcagaattca atatctgctt    1860
tcactcacgg acagaaagac tgtttagagt gctttcccgt tcagaatctc aacccgtttc    1920
tgtcgtcaa aaaggcgtat cagaaactgt gctacattca tcatatcatg ggaaaggtgc    1980
cagacgcttg cactgcctgc gatctggtca atgtggattt ggatgactgc atctttgaac    2040
aataa                                                                 2045

SEQ ID NO: 17           moltype = DNA   length = 144
FEATURE                 Location/Qualifiers
source                  1..144
                        mol_type = other DNA
                        note = artificial sequence
                        organism = unidentified
SEQUENCE: 17
aataaacgat aacgccgttg gtggcgtgag gcatgtaaaa ggttacatca ttatcttgtt     60
cgccatccgg ttggtataaa tagacgttca tgttggtttt tgtttcagtt gcaagttggc    120
tgcggcgcgc gcagcacctt tgcg                                           144

SEQ ID NO: 18           moltype = DNA   length = 92
FEATURE                 Location/Qualifiers
source                  1..92
                        mol_type = other DNA
                        note = artificial sequence
                        organism = unidentified
SEQUENCE: 18
atcatggaga taattaaaat gataaccatc tcgcaaataa ataagtattt tactgttttc     60
gtaacagttt tgtaataaaa aaacctataa at                                   92

SEQ ID NO: 19           moltype = DNA   length = 2222
FEATURE                 Location/Qualifiers
source                  1..2222
                        mol_type = other DNA
                        note = artificial sequence
                        organism = unidentified
SEQUENCE: 19
aataaacgat aacgccgttg gtggcgtgag gcatgtaaaa ggttacatca ttatcttgtt     60
```

```
cgccatccgg ttggtataaa tagacgttca tgttggtttt tgtttcagtt gcaagttggc    120
tgcggcgcgc gcagcacctt tgcgggatcc tcaggtagta agtattcatt gtaaatctga    180
tattatttgt attattatac ctacctaatt tgcagtgcag atcatggaga taattaaaat    240
gataaccatc tcgcaaataa ataagtattt tactgttttc gtaacagttt tgtaataaaa    300
aaacctataa atcccattac ggcagtataa attcgttcat tttggatatt gtttcagtgc    360
cggggtttta cgagattgtg attaaggtcc ccagcgacct tgacgggcat ctgcccggca    420
tttctgacag ctttgtgaac tgggtggccg agaaggagtg ggagttgccg ccagattctg    480
acttggatct gaatctgatt gagcaggcac ccctgaccgt ggccgagaag ctgcagcgcg    540
actttctgac ggagtggcgc cgtgtgagta aggcccggag ggcccttttc tttgtgcaat    600
ttgagaaggg agagagctac ttccacttac acgtgctcgt ggaaaccacc ggggtgaaat    660
ccttagtttt gggacgtttc ctgagtcaga ttcgcgaaaa actgattcag agaatttacc    720
gcgggatcga gccgactttg ccaaactggt tcgcggtcac aaagaccaga aacggcgccg    780
gaggcgggaa caaggtggtg gacgagtgct acatccccaa ttacttgctc cccaaaaccc    840
agcctgagct ccagtgggcg tggactaatt tagaacagta tttaagcgcc tgtttgaatc    900
tcacggagcg taaacggttg gtggcgcagc atctgacgca cgtgtcgcag acgcaggagc    960
agaacaaaga gaatcagaat cccaattctg acgcgccggt gatcagatca aaaacttcag   1020
ccaggtacat ggagctggtc gggtggctcg tggacaaggg gattacctcg agaagcagt   1080
ggatccagga ggaccaggcc tcatacatct ccttcaatgc ggcctccaac tcgcggtccc   1140
aaatcaaggc tgccttggac aatgcgggaa agattatgag cctgactaaa accgcccccg   1200
actacctggt gggccagcag cccgtggagg acatttccag caatcggatt tataaaattt   1260
tggaactaaa cgggtacgat ccccaatatg cggcttccgt ctttctggga tgggccacga   1320
aaaagttcgg caagaggaac accatctggc tgtttgggcc tgcaactacc gggaagacca   1380
acatcgcgga ggcctatagcc cacactgtgc ccttctacgg gtgcgtaaac tggaccaatg   1440
agaactttcc cttcaacgac tgtgtcgaca agatggtgat ctggtgggag aggggaaga   1500
tgaccgccaa ggtcgtggag tcggccaaag ccattctcgg aggaagcaag gtgcgcgtgg   1560
accagaaatg caagtcctcg gcccagatag acccgactcc cgtgatcgtc acctccaaca   1620
ccaacatgtg cgccgtgatt gacgggaact caacgacctt cgaacaccag cagccgttgc   1680
aagaccggat gttcaaattt gaactcaccc gccgtctgga tcatgacttt gggaaggtca   1740
ccaagcagga agtcaaagac ttttttccggt gggcaaagga tcacgtggtt gaggtggagc   1800
atgaattcta cgtcaaaaag ggtggagcca agaaaagacc cgccccagt gacgcagata   1860
taagtgagcc caaacgggtg cgcgagtcag ttgcgcagcc atcgacgtca gacgcggaag   1920
cttcgatcaa ctacgcagac aggtaccaaa acaaatgttc tcgtcacgtg ggcatgaatc   1980
tgatgctgtt tccctgcaga caatgcgaga gaatgaatca gaattcaaat atctgcttca   2040
ctcacggaca gaaagactgt ttagagtgct ttcccgtgtc agaatctcaa cccgtttctg   2100
tcgtcaaaaa ggcgtatcag aaactgtgct acattcatca tatcatggga aaggtgccag   2160
acgcttgcac tgcctgcgat ctggtcaatg tggattggga tgactgcatc tttgaacaat   2220
aa                                                                  2222

SEQ ID NO: 20         moltype = DNA   length = 328
FEATURE               Location/Qualifiers
source                1..328
                      mol_type = other DNA
                      note = artificial sequence
                      organism = unidentified
SEQUENCE: 20
cacatgttgg acatcgtgtc gtttgagcgt ataaagaat atataagagc taatttaggc      60
catttcacag taatcaccga caaatgttcg aagcgtaaag tgtgtcttca tcacaaacga    120
attgccaggt tgttgggcat taaaaaaata tatcatcaag aatacaaacg ggttgtttca    180
aaggtttaca agaagcaaac attgtaaacg tgccggagca acaatctccg gagactgcgg    240
ccgtgtgcaa aaattaaaag ctgttgaata aactggaatc gagctcttac aacaaatcca    300
acattgacca gctggccgtt attgtaaa                                       328

SEQ ID NO: 21         moltype = DNA   length = 59
FEATURE               Location/Qualifiers
source                1..59
                      mol_type = other DNA
                      note = artificial sequence
                      organism = unidentified
SEQUENCE: 21
gggagttcag tcgtcgaatg caaaacgtaa aaatattaa taaggtaaaa actacagct       59

SEQ ID NO: 22         moltype = DNA   length = 110
FEATURE               Location/Qualifiers
source                1..110
                      mol_type = other DNA
                      note = artificial sequence
                      organism = unidentified
SEQUENCE: 22
gacctttaat tcaacccaac acaatatatt atagttaaat aagaattatt atcaaatcat      60
ttgtatatta attaaaatac tatactgtaa attacatttt atttacaatc                110

SEQ ID NO: 23         moltype = DNA   length = 2114
FEATURE               Location/Qualifiers
source                1..2114
                      mol_type = other DNA
                      note = artificial sequence
                      organism = unidentified
SEQUENCE: 23
atcatggaga taattaaaat gataaccatc tcgcaaataa ataagtattt tactgttttc      60
```

-continued

```
gtaacagttt tgtaataaaa aaacctataa atattccgga ttattcatac cgtcccacca    120
tcggcgcgg atcctcaggt agtaagtatt cattgtaaat ctgatattat ttgtattatt     180
atacctacct aatttgcagt gcagcccatt acggcagtat aaattcgttc attttggata    240
ttgtttcagt gccggggttt tacgagattg tgattaaggt ccccagcgac cttgacgggc    300
atctgcccgg catttctgac agctttgtga actgggtggc cgagaaggag tgggagttgc    360
cgccagattc tgacttggat ctgaatctga ttgagcaggc accctgacc gtggccgaga     420
agctgcagcg cgactttctg acggagtggc gccgtgtgag taaggcccg gaggccctt     480
tctttgtgca atttgagaag ggagagagct acttccactt acacgtgctc gtggaaacca   540
ccggggtgaa atccttagtt ttgggacgtt tcctgagtca gattcgcgaa aaactgattc    600
agagaattta ccgcgggatc gagccgactt tgccaaactg gttcgcggtc acaaagacca    660
gaaacggcgc cggaggcggg aacaaggtgg tggacgagtg ctacatcccc aattacttgc    720
tccccaaaac ccagcctgag ctccagtggg cgtggactaa tttagaacag tatttaagcg    780
cctgtttgaa tctcacggag cgtaaacggt tggtggcgca gcatctgacg cacgtgtcgc    840
agacgcagga gcagaacaaa gagaatcaga atcccaattc tgacgcgccg gtgatcagat    900
caaaaacttc agccaggtac atggagctgg tcgggtggct cgtggacaag gggattacct    960
cggagaagca gtggatccag gaggaccagg cctcatacat ctccttcaat gcggcctcca   1020
actcgcggtc ccaaatcaag gctgccttgg acaatgcggg aaagattatg agcctgacta   1080
aaaccgcccc cgactacctg gtgggccagc agcccgtgga ggacattcc agcaatcgga   1140
tttataaat tttggaacta aacgggtacg atcccaata tgcggcttcc gtctttctgg     1200
gatgggccac gaaaagttc ggcaagagga acaccatctg gctgtttggg cctgcaacta   1260
ccgggaagac caacatcgcg gaggccatag cccacactgt gcccttctac gggtgcgtaa   1320
actggaccaa tgagaacttt cccttcaacg actgtgtcga caagatggtg atctggtggg   1380
aggaggggaa gatgaccgcc aaggtcgtgg agtcggccaa agccattctc ggaggaagca   1440
aggtgcgcgt ggaccagaaa tgcaagtcct cggcccagat agaccgact cccgtgatcg    1500
tcacctccaa caccaacatg tgcgccgtga ttgacgggaa ctcaacgacc ttcgaacacc   1560
agcagccgtt gcaagaccgg atgttcaaat ttgaactcac ccgccgtctg gatcatgact   1620
ttgggaaggt caccaagcag gaagtcaaag acttttttccg gtgggcaaag gatcacgtgg   1680
ttgaggtgga gcatgaattc tacgtcaaaa agggtggagc caagaaaaga cccgccccca   1740
gtgacgcaga tataagtgag cccaaacggg tgcgcgagtc agttgcgcag ccatcgacgt   1800
cagacgcgga agcttcgatc aactacgcag acaggtacca aaacaaatgt tctcgtcacg   1860
tgggcatgaa tctgatgctg ttttccctgca gacaatgcga gagaatgaat cagaattcaa   1920
atatctgctt cactcacgga cagaaagact gtttagagtg ctttcccgtg tcagaatctc   1980
aacccgtttc tgtcgtcaaa aaggcgtatc agaaactgtg ctacattcat catatcatgg   2040
gaaaggtgcc agacgcttgc actgcctgcg atctggtcaa tgtggatttg gatgactgca   2100
tctttgaaca ataa                                                     2114
```